(12) United States Patent
Fisker et al.

(10) Patent No.: US 11,020,204 B2
(45) Date of Patent: Jun. 1, 2021

(54) VIRTUALLY DESIGNING A CUSTOMIZED HEALING ABUTMENT

(71) Applicant: 3Shape A/S, Copenhagen K (DK)

(72) Inventors: Rune Fisker, Virum (DK); Anders Kjaer-Nielsen, Frederiksberg (DK)

(73) Assignee: 3SHAPE A/S, Copenhagen (DK)

( * ) Notice: Subject to any disclaimer, the term of this patent is extended or adjusted under 35 U.S.C. 154(b) by 1007 days.

(21) Appl. No.: 14/367,591

(22) PCT Filed: Dec. 19, 2012

(86) PCT No.: PCT/EP2012/076204
§ 371 (c)(1),
(2) Date: Jun. 20, 2014

(87) PCT Pub. No.: WO2013/092744
PCT Pub. Date: Jun. 27, 2013

(65) Prior Publication Data
US 2015/0025855 A1 Jan. 22, 2015

Related U.S. Application Data

(60) Provisional application No. 61/578,603, filed on Dec. 21, 2011.

(30) Foreign Application Priority Data

Dec. 21, 2011 (DK) .......................... PA 2011 00989

(51) Int. Cl.
*A61C 1/08* (2006.01)
*A61C 8/00* (2006.01)
(Continued)

(52) U.S. Cl.
CPC ............... *A61C 1/082* (2013.01); *A61B 6/14* (2013.01); *A61C 1/084* (2013.01); *A61C 8/008* (2013.01);
(Continued)

(58) Field of Classification Search
CPC ..... A61C 1/082; A61C 13/0004; A61C 9/004; A61C 8/008; A61C 8/0077; A61C 1/084; G06F 17/50; A61B 6/14
(Continued)

(56) References Cited

U.S. PATENT DOCUMENTS

2008/0153067 A1* 6/2008 Berckmans .......... A61C 8/0089
433/213
2008/0286722 A1 11/2008 Berckmans, III et al.
(Continued)

FOREIGN PATENT DOCUMENTS

CN 2636834 9/2004
CN 101530349 9/2009
(Continued)

OTHER PUBLICATIONS

Office Action (Notification of Reasons for Refusal) dated Sep. 20, 2016, by the Japanese Patent Office in corresponding Japanese Patent Application No. 2014-547984 and an English Translation of the Office Action. (15 pages).
(Continued)

*Primary Examiner* — Saif A Alhija
(74) *Attorney, Agent, or Firm* — Buchanan Ingersoll & Rooney PC

(57) ABSTRACT

A method of virtually designing a customized healing abutment and a drill guide for a patient, where the method includes: obtaining a CT scan including at least part of the patient's jaw bone; virtually placing at least one implant relative to the jaw bone of the CT scan, such that a planned implant placement is defined; virtually designing: a drill guide for guiding the surgical drilling of a bore for the implant into the patient's jaw bone at the planned implant placement; and a customized healing abutment configured for shaping the soft tissue according to a target profile when
(Continued)

arranged in the implant; where the design of the drill guide and of the customized healing abutment is at least partly based on the CT scan and on the planned implant placement.

29 Claims, 24 Drawing Sheets

(51) Int. Cl.
    *A61C 9/00*         (2006.01)
    *G06F 30/00*       (2020.01)
    *A61C 13/00*       (2006.01)
    *A61B 6/14*         (2006.01)
    *G16H 20/40*       (2018.01)

(52) U.S. Cl.
    CPC ............ *A61C 8/0077* (2013.01); *A61C 9/004* (2013.01); *A61C 13/0004* (2013.01); *G06F 30/00* (2020.01); *G16H 20/40* (2018.01)

(58) Field of Classification Search
    USPC ........................................................ 703/1, 11
    See application file for complete search history.

(56) References Cited

U.S. PATENT DOCUMENTS

| | | | |
|---|---|---|---|
| 2009/0087817 A1* | 4/2009 | Jansen | A61C 13/34 433/223 |
| 2009/0092946 A1 | 4/2009 | Yau et al. | |
| 2009/0111071 A1 | 4/2009 | Yau et al. | |
| 2009/0149977 A1 | 6/2009 | Schendel | |
| 2010/0105011 A1* | 4/2010 | Karkar | A61C 13/0004 433/215 |
| 2011/0276159 A1 | 11/2011 | Chun et al. | |
| 2012/0115105 A1 | 5/2012 | Schneider | |
| 2012/0143364 A1 | 6/2012 | McLeod et al. | |

FOREIGN PATENT DOCUMENTS

| | | |
|---|---|---|
| CN | 101365395 | 8/2010 |
| CN | 101803957 | 8/2010 |
| CN | 102159155 | 8/2011 |
| EP | 1 362 560 A1 | 11/2003 |
| EP | 2 343 025 A2 | 7/2011 |
| JP | 2003-325552 A | 11/2003 |
| JP | 2005-296497 A | 10/2005 |
| JP | 2009-90097 A | 4/2009 |
| JP | 2011-143247 A | 7/2011 |
| KR | 100912271 B1 | 8/2009 |
| KR | 2010-0036269 | 4/2010 |
| KR | 20110132825 | 12/2011 |
| WO | 2009007401 | 1/2009 |
| WO | WO 2010/108935 A1 | 9/2010 |
| WO | WO 2011/157762 A2 | 12/2011 |

OTHER PUBLICATIONS

Second Office Action issued in corresponding Chinese Patent Application No. 201280070372.0, dated Feb. 4, 2017, with English Translation (16 pages).

International Search Report (PCT/ISA/210) dated Apr. 26, 2013 by the European Patent Office as the International Searching Authority for International Application No. PCT/EP2012/076204.

Notice of Reasons for Rejection issued in corresponding Japanese Patent Application No. 2018-038917, dated May 7, 2019 (9 pages).

Summons to Attend Oral Proceedings issued in corresponding European Patent Application No. 12 808 812.7, dated Aug. 25, 2020 (6 pages).

Mee-Kyoung Son et al. "Gingival recontouring by provisional implant restoration for optimal emergence profile: report of two cases", Journal of Periodontal & Implant Science, Dec. 31, 2011; 13 pages.

Office Action issued in corresponding Brazilian Patent Application No. BR112014015343-4, dated Mar. 25, 2020 (4 pages).

Office Action issued in corresponding Chinese Patent Application No. 201260070372.0, dated Jun. 2, 2016, with English translation (25 pages).

Notice of Allowance issued in corresponding Korean Patent Application No. 10-2014-7020255, dated Mar. 3, 2020, with English Translation (3 pages).

\* cited by examiner

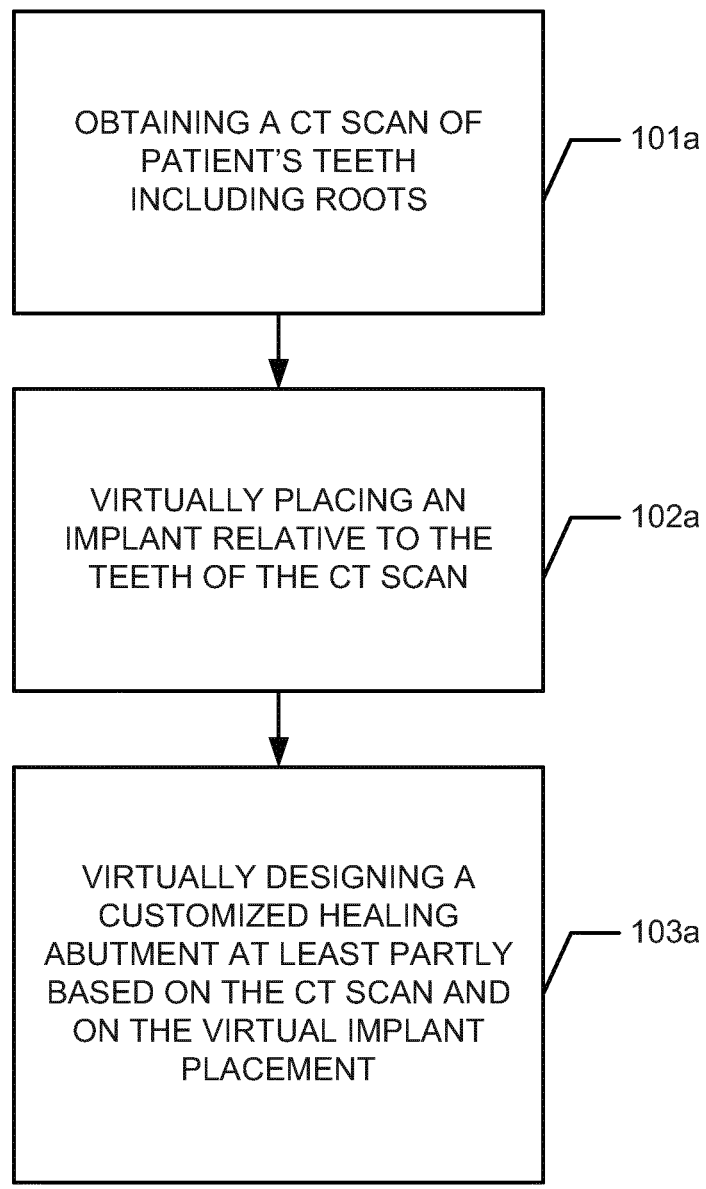

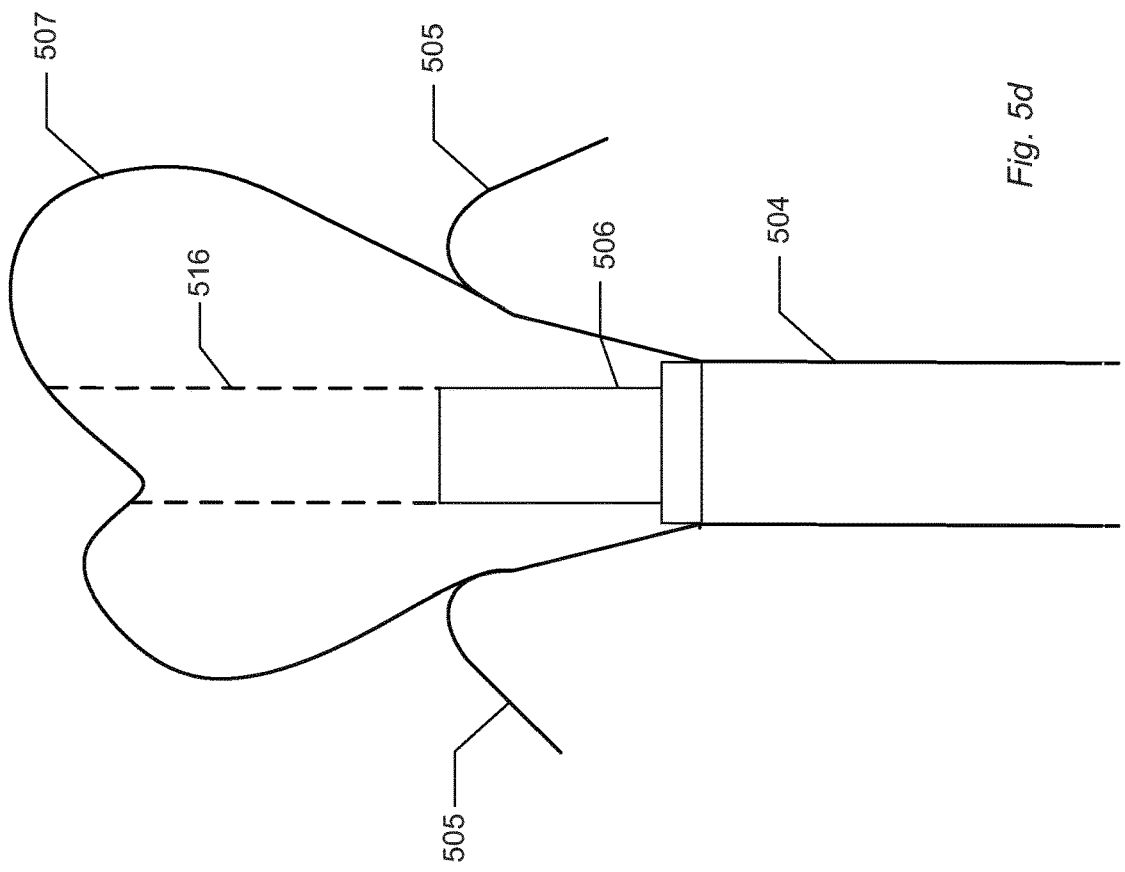
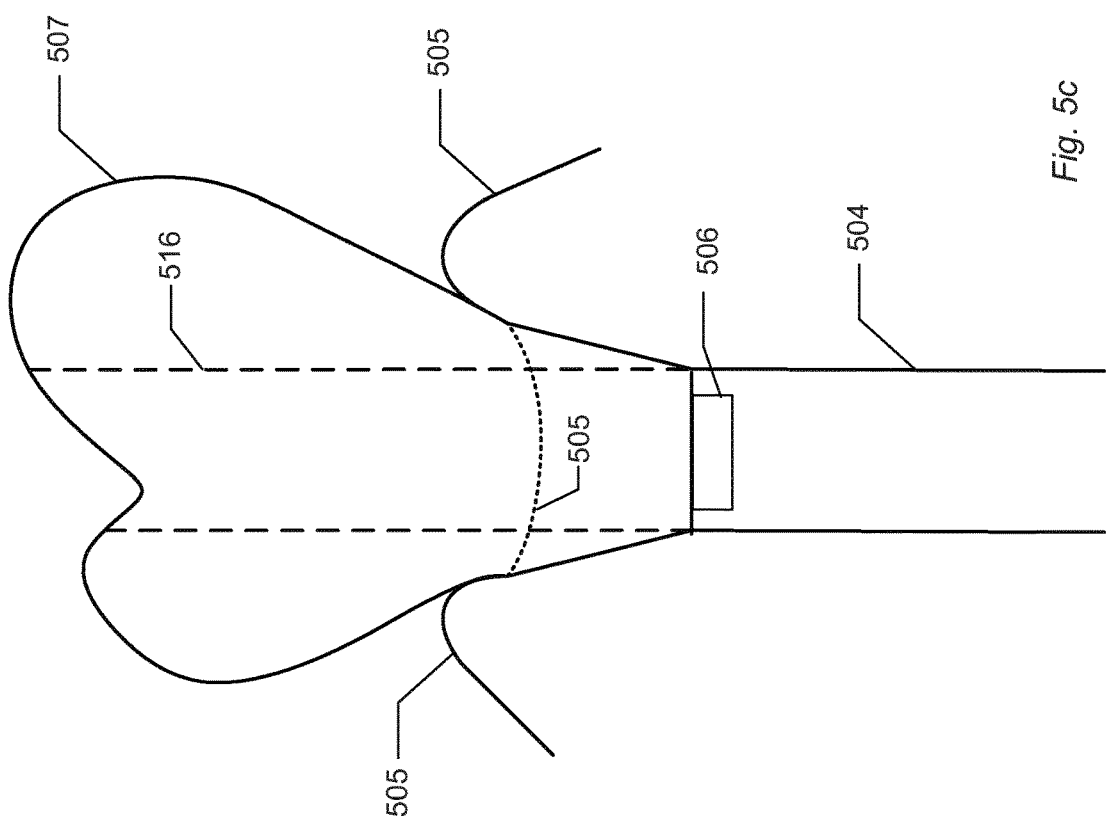

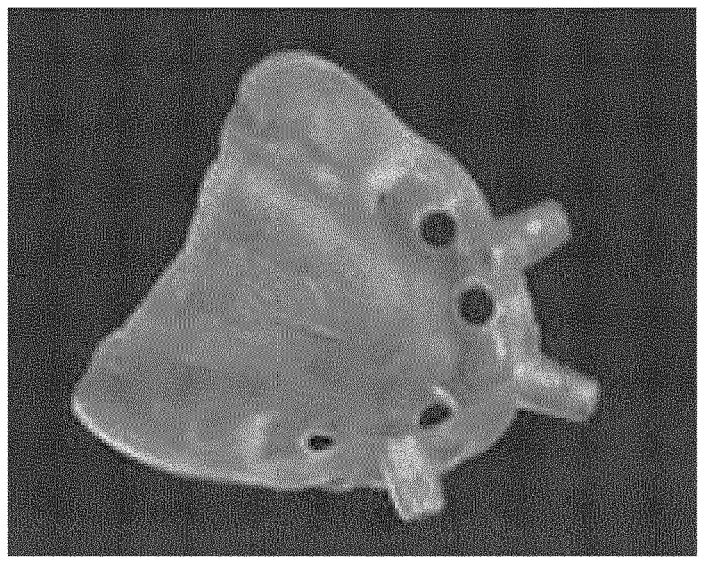
Fig. 14a)
Fig. 14b)
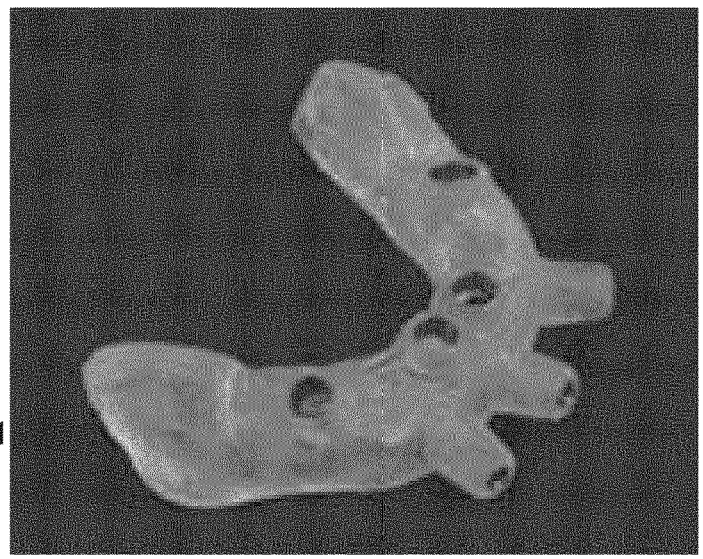
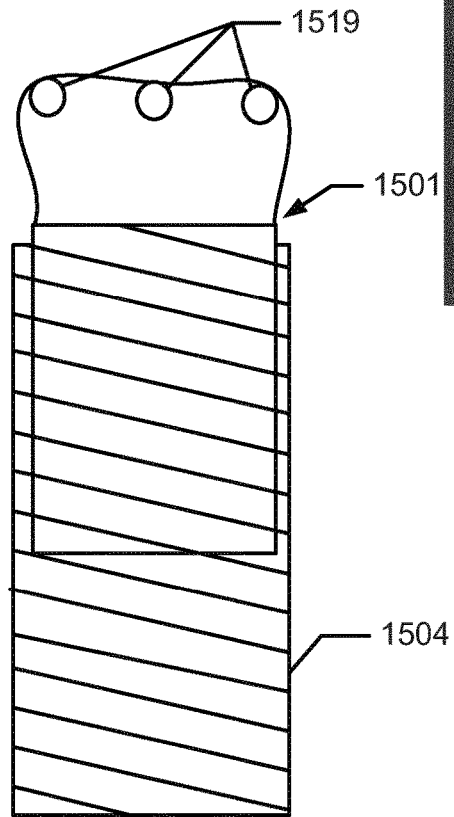
Fig. 15

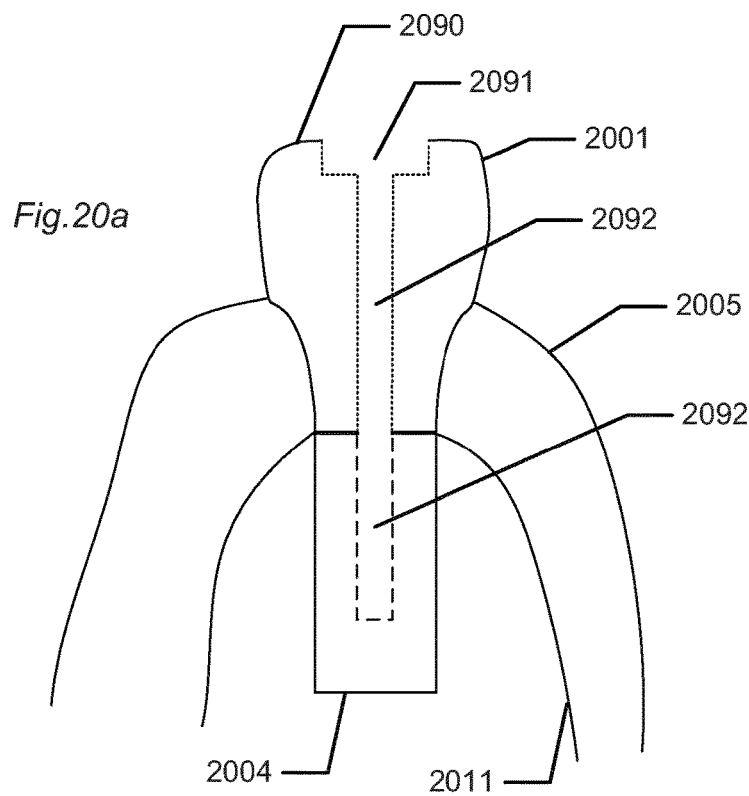
Fig.20a
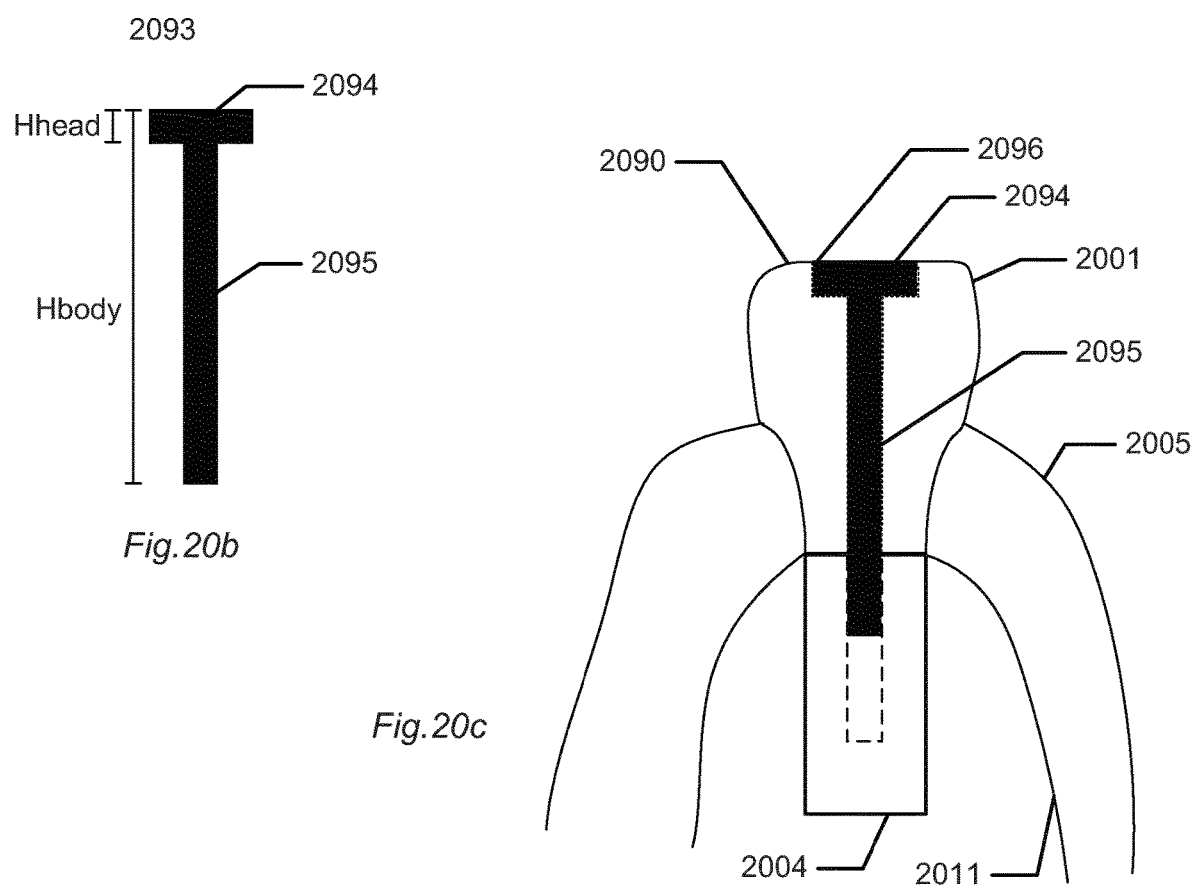
Fig.20b
Fig.20c

VIRTUALLY DESIGNING A CUSTOMIZED HEALING ABUTMENT

FIELD OF THE INVENTION

This invention generally relates to a system and a method for virtually designing a customized healing abutment for a patient. In particular, the invention relates to a system, a user interface and a method for virtually designing a drill guide and a customized healing abutment for a patient.

BACKGROUND OF THE INVENTION

Dental prosthetic procedures for replacing one or more teeth with dental restorations, such as crowns and bridges, are performed on a daily basis by dentists worldwide. In cases where a patient's original tooth is either missing or is ill or damaged to an extent where it no longer can serve as the support for a dental restoration, the dentist may decide to place an implant in the patient's jaw bone, such that the dental restoration can be supported by this implant e.g. via an implant abutment. When arranged in the patient's mouth implants can replace the parts of the teeth which are not visible in a 3D surface scan, such as the roots of the tooth. If the original tooth or any remains of it still are present in the patient's mouth these are extracted and a bore for the implant is drilled into the jaw bone. The implant is placed in this bore and the surrounding bone grows into very close apposition to the implant such that the implant is secured to the bone. This process is also known as osseointegration. In particular titanium has shown to have very good osseointegration properties and is currently the most preferred material to use for implants. When osseointegration is complete and the implant is secured in the bone it may subsequently be used as support for dental restorations. Typically implant abutments are placed in the implant to serve as an interface between the implant and the final restoration which may comprise an anatomical part of the dental restoration, such as a crown or a bridge, and coping layers.

Osseointegration usually takes several months to complete and during that period of time a healing abutment can be placed at the implant in order to e.g. ensure that the implant is kept free of dirt and food. The healing abutment can further be used for shaping the soft tissue in the region where the original tooth was extracted from such that the soft tissue maintains an anatomically correct shape instead of collapsing into the space which previously was occupied by the extracted tooth.

Once the osseointegration is completed, the healing abutment is removed and the final restoration is arranged in the implant, e.g. by securing an implant abutment in the implant using an implant screw and cementing the final restoration to the implant abutment.

WO2011157762 discloses a computer based method is used to design a healing cap of an implant. The method is based on a 3D computer plan of the implant comprising digital representations of positions of implants in the mouth of the patient. The method comprises loading the 3D implant plan into a computer and combining the 3D implant plan with information about a prosthetic setup. The method determines a marginal edge of a healing cap of an implant based on a 3D representation of the existing patient anatomy, the 3D implant plan and the prosthetic set-up. The healing cap is then manufactured to the custom design.

US20120115105 discloses a gingiva former, which has a connecting geometry to an implant and comprises a tailor-made edge, a tapering lower part that is located beneath and has a tailor-made shape, and a tapering upper part having a lateral surface, wherein the lateral surface has an angle of inclination of between 0.5° and 30° with respect to a longitudinal axis of the connecting geometry.

US 2009/0111071 discloses a method for designing a digital abutment for a dental implant includes the steps of: a) implant planning where implant planning is initiated based on digital data obtained from the patient and loaded into a computer system to enable an implant fixture to be implanted at the implant site in the best position, b) establishment of digital reference abutment where a digital reference abutment is established at the implant site and positioned on the implant fixture, c) adjustment of the digital reference abutment where the digital reference abutment has a sub-gingival part and a supra-gingival part at the top side of the sub-gingival part, and the angle between the sub-gingival part and the supra-gingival part is adjusted based on the best prosthesis position, and d) finish of digital abutment where the digital reference abutment becomes a digital abutment for placement after the adjustment.

For the surgical drilling of a bore into the patient's jaw bone for the implant, a drill guide can be arranged in the patient's mouth where it guides the dentist to drill the bore at a planned implant placement. The drill guide can be designed based on a CT scan of the patient's teeth and be manufactured using direct digital manufacturing techniques. US2012/0143364 discloses a dental CAD/CAM system which forms a custom dental preparation guide for guiding a dental tool that alters a shapes a tooth structure to which a custom prosthetic dental item is to be attached. The system acquires an optical measurement and an x-ray of at least one dental structure. The system correlates the acquired optical measurement and the x-ray to form a model of the at least one dental structure. The system generates a model of a reduced tooth structure based on the model of the at least one dental structure. The system also provides at least one dental preparation guide based on the model of the reduced tooth structure.

However, it remains to disclose a method, a user interface and a system for designing a drill guide and a customized healing abutment for a patient where the virtual design of the drill guide and the customized healing abutment at least partly is based on the CT scan and on the planned implant placement. Such a method, user interface and system can provide that both the drill guide and the customized healing abutment can be designed and subsequently manufactured before the surgical drilling of a bore into the patient's jaw bone.

SUMMARY

Disclosed is a method of virtually designing a customized healing abutment and a drill guide for a patient, where the method comprises:
 obtaining a CT scan comprising at least part of the patient's jaw bone;
 virtually placing at least one implant relative to the jaw bone in the CT scan such that a planned implant placement is defined; and
 virtually designing:
  a drill guide for guiding the surgical drilling of a bore for the implant into the patient's jaw bone at the planned implant placement; and
  a customized healing abutment configured for shaping the soft tissue according to a target profile when arranged in the implant;

where the design of the drill guide and of the customized healing abutment is at least partly based on the CT scan and on the planned implant placement.

For the drill guide, the apertures of the drill guide through which the surgical drill engages the patient's jaw bone can be virtual designed based on the CT scan and the planned implant placement. The virtual designing can also relate to the portions of the drill guide which are shaped to arrange the drill guide correctly in the patient's mouth, e.g. relative to the patient's teeth if he has any in his mouth.

For the customized healing abutment, the shape of the outer surface can be can be virtual designed based on the CT scan and the planned implant placement, where the virtual designing preferably is such that the manufactured customized healing abutment can shape the gingiva according to the target profile when arranged in the implant.

The designing of the drill guide and the customized healing abutment is based on the same CT scan, such as a preoperational CT scan obtained before the surgical drilling into the patient's jaw bone in contrast to prior art methods where a second scan is acquired for virtually designing the customized healing abutment.

The phrase "CT scan" is an often used medical abbreviation for Computerized Tomography or Computerized Axial Tomography which is an X-ray procedure that combines many X-ray images with the aid of a computer to generate cross-sectional views and 3D images of the internal organs and structures of the body, such as the teeth and jaw bone of a patient. A CT scan can be used to define structures in the body and/or assist in procedures by helping to accurately guide the placement of instruments or treatments.

The customized healing abutment is a personalized component configured for being arranged in relation to a dental implant with the surface facing away from the implant, herein often referred to as the uppermost surface, preferably being substantially flat. The uppermost surface can be substantially flat by itself, such as when a screw for securing the customized healing abutment in the implant is an integrated part of the customized healing abutment. When a non-integrated implant screw is used for securing the customized healing abutment in the implant, the uppermost surface defined by the customized healing abutment and the implant screw is preferably substantially flat with the only indentation in the surface being defined by indentations of the screw.

When using the phases "lower" and "upper" to describe the arrangement of objects relative to the jaw bone of the patient, the phase "lower" is used in relation to the portion of the object facing towards the jaw bone, while the phase "upper" is used in relation to the portion of the object facing away from the jaw bone. I.e. when an object, such as the customized healing abutment, is arranged relative to the patient's upper jaw and the patient is sitting up, the upper part of the object is closer to the floor than the lower part.

As will be understood herein when referring to the different parts, i.e. the drill guide and the customized healing abutment in relation to the design method as disclosed, it is not a physical part as such, but a virtual representation of a physical part which is described. However, with respect to the final product this will comprise physical parts which have been provided by manufacturing the specific parts, e.g. using direct digital manufacture methods such as 3D printing, based on the virtual representation established during the design process.

The implant which is virtually placed relative to the jaw bone in the CT scan is a virtual representation of a physical implant adapted for replacing an original tooth root in the jaw bone of the patient. The virtual representation can e.g. be a CAD model of the implant or an indication of the implant using full lines or a contour of the implant.

The virtually designed drill guide is a virtual representation of a physical drill guide adapted for being arranged in the patient's mouth to guide surgical drilling of a bore into the patient's jaw bone. Virtually designing the drill guide based on the planned implant placement provides the advantage that a physical implant placed in the bore drilled using the manufactured drill guide is arranged according to the planned implant placement. The physical drill guide can be manufactured from the virtual representation of the drill guide using e.g. 3D printing.

Likewise the virtually designed customized healing abutment is a virtual representation of a physical customized healing abutment. A physical customized healing abutment manufactured from the virtually representation of the customized healing abutment is adapted for allowing soft tissue at the implant to heal properly before attachment of a final restoration in the implant. During the healing of the soft tissue, the customized healing abutment prevents the soft tissue from collapsing into the space previously occupied by the extracted tooth, such that when the osseointegration of the implant is completed, the soft tissue is shaped according to the target shape.

When the customized healing abutment is arranged in the implant its outer surface can engage the soft tissue at the implant and shape it to follow the emergence profile of the customized healing abutment. In some embodiments, the emergence profile of the customized healing abutment is at least partly designed based on the target profile. For example, the emergence profile may be set to be identical to the target profile at least over a portion of the soft tissue engaging surface of the customized healing abutment. The target profile of the soft tissue can be selected from a library or it can be derived from the shape of a previous tooth or from the shape of a final restoration designed to be placed at the implant. The target profile can be defined relative to an axis or a plane of the patient's set of teeth, such as the occlusal plane, a normal to the occlusal plane or the longitudinal axis of the tooth that the implant and restoration are replacing.

One advantage of taking the planned implant placement into account when virtually designing the drill guide and the customized healing abutment is that the drill guide and the customized healing abutment can be designed based on a placement of the implant which is very likely to provide a good anchoring of the implant and hence the attached final restoration to the patient's jaw bone. Without a CT scan to indicate where it is likely to obtain a good implant-jaw bone connection the subsequent designing of the drill guide and the customized healing abutment may be far from ideal.

Consequently, it is an advantage of the method that a customized healing abutment and a drill guide can be virtually designed, e.g. by means of the method being computer-implemented. It is an advantage that the method may provide a better and faster result of the design. Further it is an advantage that the customized healing abutment and the drill guide can easily be manufactured based on the virtual designs, and the manufacturing cost of the customized healing abutment and the drill guide may be lower than for a manually manufactured customized healing abutment and a manually manufactured drill guide.

Consequently, it is an object of the present invention to provide a method, a system and a user interface which provides the possibility of designing and manufacturing the drill guide to the dentist together with the customized healing abutment, such that when the bore has been drilled into the patient's jaw bone assisted by the drill guide, the customized healing abutment is already available and can be inserted into an implant arranged in the drilled bore. This saves the patient for a visit at the dentist compared to the cases where the customized healing abutment is virtually designed after the surgical drilling, e.g. based on an additional scan obtained with a scan flag arranged in the implant to derive the position and orientation of the implant relative to the patient's teeth and/or jaw bone. In such cases, the patient must visit the dentist one more time to have the customized healing abutment inserted in the implant. Besides taking time for the patient and the dentist, this also involves significant additional discomfort when the customized healing abutment is inserted into the implant to replace any temporary component arranged there, such as a mass manufactured healing abutment.

It is an object of the present invention to provide a method, a system and a user interface for designing a customized healing abutment for the patient.

It is an object of the present invention to provide a method, a system and a user interface for designing a customized healing abutment for a patient where the uppermost surface of the customized healing abutment has a smooth surface.

Disclosed is a method of virtually designing a customized healing abutment for a patient, where the method comprises:
  obtaining a CT scan comprising at least part of the patient's teeth including teeth roots;
  virtually placing at least one implant relative to the teeth of the CT scan; and
  virtually designing a customized healing abutment, where the design of the customized healing abutment is at least partly based on the CT scan and on the virtual implant placement.

Consequently, it is an advantage of the method that a customized healing abutment can be virtually designed, e.g. by means of the method being computer-implemented. It is an advantage that the method may provide a better and faster result of the design of the customized healing abutment. Further it is an advantage that the customized healing abutment can easily be manufactured based on the virtual design, and the manufacturing cost of the customized healing abutment may be lower than for a manually manufactured customized healing abutment.

In a CT scan, the teeth, both the visible part above the soft tissue, such as the gingiva, and the non-visible part, i.e. the teeth roots, below the gingiva, and jaw bones and nerves are captured or acquired. However, soft tissue, such as gingiva, may also be captured or derived from a CT scan.

It is an advantage that the customized healing abutment and the drill guide can be designed based on the CT scan comprising the jaw bone and/or neighbor teeth and on the planned implant placement, e.g. position and/or orientation, of the implant relative to the patient's jaw bone and/or teeth. The virtually designing can then be adapted to provide that the manufactured customized healing abutment is aligned and shaped such that it can shape the surrounding soft tissue according the target profile when it is attached to the implant.

In some embodiments, the implant is virtually placed in the position in the patient's dental arch, where an original tooth used to be, e.g. before extraction. I.e. the implant is virtually placed in the part of the CT scan where the roots of the original tooth used to be. This may be advantageous when the jaw bone is healthy and the implant is arranged to support a restoration with a shape similar to the shape of the original tooth.

In the patient's mouth the customized healing abutment will be attached to the implant, e.g. by means of a screw in the customized healing abutment which is adapted to be screwed into a screw hole in the implant. Alternatively, the implant comprises a screw, and the customized healing abutment comprises a screw hole into which the screw from the implant fits.

The virtual design of the customized healing abutment and the drill guide may be performed by means of 3D modeling, which is the process of developing a mathematical, wireframe representation of any three-dimensional object, called a 3D model, via specialized software. Models may be created automatically, e.g. 3D models may be created using multiple approaches: use of NURBS curves to generate accurate and smooth surface patches, polygonal mesh modeling which is a manipulation of faceted geometry, or polygonal mesh subdivision which is advanced tessellation of polygons, resulting in smooth surfaces similar to NURBS models.

In some embodiments the method comprises obtaining a 3D surface scan comprising at least part of the teeth and at least part of the soft tissue of the patient's mouth.

Preferably, the part of the of the teeth and at least part of the soft tissue of the patient's mouth obtained in the 3D surface scan overlaps at least partially with the obtained CT scan, i.e. the CT scan and the 3D surface scan has captured identical portions of the patient's oral cavity.

It is an advantage to obtain a 3D surface scan of the visible parts of the teeth and gingiva, because the edge between gingiva and teeth may be more clear and distinct in a 3D surface scan than in a CT scan, and the distinct edge between gingiva and teeth may provide that the design of especially the customized healing abutment is easier to perform and with a better result. Further, many commercially available 3D surface scanners, such as the 3Shape TRIOS intra-oral scanner, are capable of obtaining data with a higher spatial resolution and precision than what can be obtained using currently available CT scanners.

In some embodiments the method comprises performing an alignment of the CT scan and the 3D surface scan before designing the customized healing abutment and/or the drill guide. The customized healing abutment and/or the drill guide can then be designed based on the aligned CT and 3D surface scans.

It is an advantage to align the CT scan and the 3D surface scan before designing any components, such as the customized healing abutment and the drill guide, because different information can be derived from the different scans, and combining the information may result in that all possible available information is gathering in one view, which provides an ideal basis for designing components.

In some embodiments, the drill guide is designed based on the CT scan alone while the customized healing abutment is designed based on the aligned CT and 3D surface scans.

In some embodiments, the customized healing abutment is designed based on the CT scan alone while the drill guide is designed based on the aligned CT and 3D surface scans.

In some embodiments the alignment comprises selecting three corresponding points on the CT scan and on the 3D surface scan.

It is an advantage to select and mark for example three points on the CT scan and three points on the 3D surface scan corresponding to each other, because by means of these corresponding points a rough alignment can be performed.

In some embodiments the alignment comprises using the computer-implemented method of iterative closets point. For example after a rough alignment has been performed using corresponding points, a fine-tuning of the rough alignment using the well-known method of iterative closest point (ICP) may be performed. Iterative Closest Point (ICP) is an algorithm employed to minimize the difference between two clouds of points. ICP may be used to reconstruct 2D or 3D surfaces from different scans, to co-register 3D models, etc. The algorithm iteratively revises the transformation, e.g. translation and/or rotation, needed to minimize the distance between the points of two raw scans. The inputs to the algorithm are points from two raw scans, initial estimation of the transformation, criteria for stopping the iteration. The output is a refined transformation.

The algorithm steps may be:

Associate points by the nearest neighbor criteria.

Estimate transformation parameters using a mean square cost function.

Transform the points using the estimated parameters.

Iterate, i.e. re-associate the points and so on.

In some embodiments, the CT scan is a preoperative CT scan obtained prior to the surgical drilling into the patient's jaw bone.

In some embodiments, the 3D surface scan is a preoperative 3D surface scan obtained prior to the surgical drilling into the patient's jaw bone.

In cases where the customized healing abutment and the drill guide are designed based on preoperational CT and 3D surface scans, a physical drill guide and a physical customized healing abutment can be manufactured from the virtual designs prior to the surgical drilling such that both are ready when the surgical drilling is to be performed.

In some embodiments the method comprises virtually placing a final restoration for the implant, i.e. virtually placing the final restoration relative to the CT scan and/or relative to the 3D surface scan. The final restoration may be a crown, a bridge, or a denture designed for being arranged at an implant abutment secured in the implant. In some cases, a coping layer is also included either as part of the final restoration or as a layer arranged between the implant abutment and the final restoration.

In some embodiment the final restoration for the implant is virtually designed.

In some embodiments the final restoration is virtually placed before virtually placing the implant.

It is an advantage to virtually place the final restoration before placing the implant and before designing the customized healing abutment, because the final restoration is the part that is visible in the mouth of the patient, and this should therefore be as visually appealing as possible and with as good functionality as possible, and this may achieved by placing the final restoration as ideally as possible in the mouth with no restrictions other than the neighbor teeth and the antagonist. This can be done by placing the final restoration first, because then no considerations regarding other dental component or parts, such as the implant, the abutment etc., should be made. After the final restoration has been virtually placed, then the implant can be virtually placed to check if there is space enough for the implant between the neighbor teeth roots, the nerves, the bones etc. and if the jaw bone is sufficiently healthy and strong to support the dental implant. With the final restoration placed relative to the jaw bone of the CT scan and/or relative to the 3D surface scan when virtually placing the implant, the operator can e.g. also evaluate which placement of the implant provides the best possibilities for designing an implant abutment which can connect the final restoration to the implant. Later the final restoration can be virtually designed to provide an improved fit to the implant position and orientation and to the implant abutment or the like.

In some embodiments the method comprises virtually designing the final restoration, such as a crown, bridge, denture.

The final restoration can be virtually designed together with the drill guide and the customized healing abutment. A final restoration manufactured from the virtually designed final restoration can be a part of the kit comprising the drill guide and the customized healing abutment.

In some embodiments the method comprises using the shape of the original tooth to design the final restoration, if the shape of the original tooth is available.

It can be an advantage to use the original shape of the tooth which the final restoration is replacing, for designing the final restoration, when the original tooth may be visually pleasing and fit to the other teeth, and the patient may prefer that the final restorations looks like the original tooth so that no one will notice that it is a restoration and not the patient's original tooth. The shape of the original tooth may be derived or obtained from a scan of the tooth, such as 3D surface scan or a CT scan of the mouth if the tooth is still present, or from an older scan of the mouth or from a 2D image, such as a photograph.

In some embodiments the design of final restoration is at least partly based on the design of the customized healing abutment.

It is an advantage to base the design of the final restoration on the design of the customized healing abutment, if the customized healing abutment has been virtually designed before the final restoration. If for example the emergence profile of the customized healing abutment is very well designed, then this emergence profile may be used in the design of the final restoration as well.

In some embodiments, the part of the design of the final restoration which is based on the design of the customized healing abutment, is the part of the design which is present sub-gingival.

In the context of the present invention, the phrases "sub-gingival" and "sub-gingivally" are used in relation to a location below a gingival surface facing into the volume of the oral cavity.

In some embodiments, the final restoration comprises a sub-gingival portion, and the sub-gingival portion is based on the design of the customized healing abutment It is an advantage for example if the emergence profile of the customized healing abutment is very well designed, then this emergence profile may be used for the final restoration as well.

In some embodiments the method comprises virtually designing a final implant abutment for insertion into the implant, where the final restoration is adapted to be attached to the final implant abutment. The final restoration can then be secured on the final abutment in the patient's mouth.

In some embodiments, the method comprises obtaining a second CT scan and/or a second 3D surface scan comprising the customized healing abutment, when placed in the mouth of the patient, and based on the second CT scan and/or the second 3D surface scan, adjusting the design of the final restoration.

In some cases it is an advantage that after the healing of the implant to the jaw bone, the patient's teeth are scanned with the customized healing abutment placed in the implant. After healing where the implant is integrated into the jaw bone via osseointegration, the implant may be fixed in the jaw bone a little different than expected and planned virtually, e.g. the implant may have moved a little to one side or may have sunken more into the jaw bone than expected. This can be detected by scanning the customized healing abutment in the implant and the surrounding teeth, as the position and orientation of the customized healing abutment will provide the position and orientation of the implant. Thereby the design of the final restoration can be adjusted based on the second scan of the customized healing abutment to take the movement of the implant in the bone into consideration, and thereby this final design of the final restoration will be as optimal as possible, as it fits to the actual situation in the mouth of the patient.

In some embodiment the drill guide and the customized healing abutment are designed simultaneously.

Designing the drill guide and the customized healing abutment simultaneously has the advantage that both components can be manufactured prior to the surgical drilling of the bore for the implant into the patient's jaw bone. The drill guide is used for guiding the drilling and when an implant is arranged in the drilled bore, the customized healing abutment can immediately be placed in the implant while the patient is still at the dentist. The drill guide and the customized healing abutment may be designed simultaneously e.g. by activating a virtual button in a user interface adapted for simultaneous designing of the two, or the drill guide and the customized healing abutment can be designed sequentially such that one is designed before the other e.g. in separate user interfaces visualized on the same visual display unit.

In some embodiments, the customized healing abutment is adapted to be arranged at least partly in the soft tissue having a desired position and orientation relative to the implant.

The customized healing abutment may be customizable partly because it can be arranged with any desired position and orientation relative to the implant. The customized healing abutment may have any desired shape such that it can be arranged with any desired position. The shape of the customized healing abutment may e.g. be a non-symmetrical shape. In some cases, the implant cannot be arranged in the patient's jaw bone in such a manner that the longitudinal axis of the implant is parallel to the longitudinal axis of the final restoration. Since the soft tissue preferably is shaped according to the final restoration and not such an angled implant, the customized healing abutment can in such cases be designed to compensate for the off-axis arrangement of the implant such that it can shape the soft tissue to be ready to fit the final restoration. Soft tissue may also be termed gingiva, sulcus, mucosa etc.

In some embodiments the design of the customized healing abutment is at least partly based on the design of the final restoration.

It is an advantage to base the design of the customized healing abutment on the design of the final restoration, if the final restoration is designed before designing the customized healing abutment. The customized healing abutment can then e.g. shape the soft tissue to have a shape which fits the emergence profile of the final restoration.

In some embodiments the design of the customized healing abutment is at least partly based on the implant placement, i.e. on the position and orientation of the implant relative to the patient's jaw bone and/or existing teeth. The placement may be the virtual planned implant placement at which the implant is virtually placed relative to the jaw bone of the CT scan.

It is an advantage to base the design of the customized healing abutment on the implant placement, i.e. position and orientation, as the customized healing abutment should fit into the implant.

In some embodiments the design of the customized healing abutment is at least partly based on a visible part of the neighbor teeth and/or on a non-visible part of the neighbor teeth.

The customized healing abutment can be placed partly in the soft tissue and partly above the soft tissue, e.g. above the gingiva. In the soft tissue the customized healing abutment should not touch or collide with the non-visible parts of the neighbor teeth which are also in the soft tissue. Above the soft tissue, the customized healing abutment should not touch or collide with the visible part of the neighbor teeth. The visible part of the neighbor teeth may be seen from the CT scan and/or 3D surface scan. The non-visible part of the neighbor teeth can be identified in the CT scan.

In some embodiments the design of the customized healing abutment is at least partly based on the soft tissue at the place where the customized healing abutment is adapted to be arranged.

Thus if the soft tissue has a specific shape which is important to maintain due to risk of infections, pain etc., then the customized healing abutment can be designed to fit and maintain the gingiva shape. The soft tissue may be represented by a part of the 3D surface scan and/or a part of the CT scan, such that the customized healing abutment at least partly is designed by shaping part of its outer surface according to the corresponding parts of the 3D surface scan and/or of the CT scan.

In some embodiments the design of the customized healing abutment is at least partly based on a target profile of the soft tissue between the implant and the final restoration. The target profile may be defined by the dentist or a dental technician based on a desired shape of the soft tissue between the implant and the final restoration.

Thus if the soft tissue around the implant and the final restoration should look or be shaped in a special way, then the customized healing abutment can be designed to provide this shape of the soft tissue, e.g. pushing the gingiva away from a neighbor teeth or allowing the gingiva to move closer to the implant top, i.e. the end of the implant pointing towards the restoration and the customized healing abutment.

The other end of the implant may be termed the bottom of the implant, which is the end pointing towards the jaw bone or the roots of the neighbor teeth.

In some embodiments the method comprises virtually designing the emergence profile of the customized healing abutment from the top of the implant to the beginning of the gingiva, i.e. to the surface of the gingiva at the gingiva-air interface. The emergence profile may be shaped according to a target profile of the soft tissue.

In some embodiments the method comprises using the shape of the original tooth to design the customized healing abutment, if the shape of the original tooth is available.

It is an advantage to use the original shape of the tooth for designing the customized healing abutment, as the design of the customized healing abutment may be an offset or cutback from the original tooth shape, for example also if the final restoration is a copy of the original tooth, which the restoration is replacing. The shape of the original tooth may be derived or obtained from a scan of the tooth, such as 3D surface scan or a CT scan of the mouth if the tooth is still present, or from an older scan of the mouth or from a 2D image, such as a photograph.

In some embodiments the designed customized healing abutment comprises a substantially flat, rounded off top.

It is an advantage to design the customized healing abutment with a flat, rounded-off top, if the customized healing abutment should be as discreet and non-visible and unnoticed as possible in the mouth of the patient. The gingiva may also heal nicely around a flat, rounded off shape, so that gingiva is in good shape when the final restoration is inserted afterwards. A flat rounded-off top also ensures that food and other materials cannot be trapped which could occur is there is a depression in the top.

In some embodiments, an uppermost surface of the customized healing abutment comprises an opening for accommodating the screw head of an implant screw by which the customized healing abutment is to be attached to an implant, and the customized healing abutment is designed to provide a smooth transition from the customized healing abutment to the implant screw.

The smooth transition may be such that no sidewall of the opening is visible when the implant screw is arranged in relation to customized healing abutment, i.e. the screw head completely covers the sidewall of the opening and the sidewall of the screw head cannot be seen. The smooth transition may be such that the uppermost surfaces of the customized healing abutment and of the implant screw head are in the same plane when the implant screw is arranged in relation to the customized healing abutment.

In some embodiments, the information relates to the height of the implant screw head, and wherein the opening of the customized healing abutment is shaped to provide that the transition from the customized healing abutment to the implant screw is smooth.

In some embodiments, the designing of the customized healing abutment comprises setting the height of the opening in the screw head at a value which provides that the screw head does not extend above the uppermost surface of the customized healing abutment or vice versa.

In some embodiments, the information relates to the length of the implant screw and wherein the customized healing abutment is designed to have a length which provides that the transition from the customized healing abutment to the implant screw is smooth.

In some embodiments, the customized healing abutment is designed to have a height is within an interval defined by the screw length.

In some embodiments, the customized healing abutment is virtually designed such that it is configured for shaping the soft tissue according to a target profile when arranged in the implant.

In some embodiments, the method comprises virtually placing at least one implant relative to the jaw bone in the CT scan such that a planned implant placement is defined.

In some embodiments the customized healing abutment is designed to be level with the surrounding soft tissue, i.e. the upper surface of the customized healing abutment is level with the soft tissue surface.

It is an advantage with a top of the customized healing abutment which is level with the surrounding soft tissue, e.g. the gingiva, because then the customized healing abutment may be more or less invisible when in the mouth of the patient.

In some embodiments the customized healing abutment is designed to have a predetermined height relative to the surrounding soft tissue.

The customized healing abutment may be designed to have a predetermined height relative to the level of the gingiva, where the top of the customized healing abutment is below the level of the gingiva, such that customized healing abutment is invisible, when in the mouth of the patient. When replacing the customized healing abutment with the final restoration, the gingiva above the customized healing abutment may be cut away to remove the customized healing abutment. Alternatively, the customized healing abutment may be designed such that its top is above the level of the gingiva, e.g. if it is uncertain how the gingiva will heal around the customized abutment, then to be on the safe side, the top of the customized healing abutment may be designed to be above the gingival level, to better direct the healing of the gingiva.

In some embodiments the design of the customized healing abutment is not adapted for attachment of a temporary crown or other temporary restoration. In some cases the customized healing abutment alone should be arranged in the implant in the healing period and no restoration should be attached to the customized healing abutment and/or the implant. The healing and fixation of the implant in the jaw bone may be improved if the implant is not affected by any forces during the healing. So if no temporary restoration is attached, then no forces from e.g. chewing food or the like should affect the implant. The customized healing abutment may e.g. have a smooth surface above the gingiva such that a temporary crown or other temporary restoration cannot be attached to it.

In some embodiments the design of the customized healing abutment comprises scan markers for deriving information of the implant position and orientation when scanning the customized healing abutment in the implant. The customized healing abutment may for example be scanned before and while inserted into the implant in the mouth of the patient. The scanning in the mouth also acquires data relating to at least a part of the patients jaw bone and/or teeth and/or soft tissue, such that the arrangement of the customized healing abutment relative to the jaw bone and/or teeth and/or soft tissue can be obtained. The customized healing abutment comprising scan markers may for example be scanned after the healing of the implant, such that the position and orientation of the implant is fixed, and such that the gingiva around the customized healing abutment has healed. Due to the scan markers on the customized healing abutment, the exact placement, i.e. position and orientation, of the implant in the jaw bone can be obtained, when the customized healing abutment is placed in the implant and scanned, such that the scan markers are captured.

The attachment of the customized healing abutment in the implant may be well-defined such that by scanning the scan marker on the customized healing abutment the exact position and orientation of the implant in the jaw bone can be obtained. The length of the customized healing abutment measured from for example the top of the implant to the highest point on the customized abutment away from the gingiva may be predefined or measured when the customized healing abutment is designed, such that the depth of the implant in the soft tissue can be calculated, when scanning the markers on the customized healing abutment.

In some embodiments the scan markers and their position on the customized healing abutment are virtually designed for matching the customized healing abutment, such that the scan markers are designed for the particular customized healing abutment.

Since the customized healing abutment is customized and unique, the scan markers may or should also be more or less customized.

In some embodiments the method comprises virtually placing the implant.

In some embodiments the implant is virtually placed after virtually placing the final restorations.

In some embodiments the method comprises virtually designing the insertion of the implant in the patient's mouth. I.e. a virtual plan or guide for the insertion may be designed, i.e. such as: the implant should be inserted downwards with an angle relative to the occlusion plane of 2 degrees etc.

In some embodiments the method comprises using the shape of the original tooth to design the planned implant placement, i.e. the planned position and orientation of the implant, if the shape of the original tooth is available. The implant position and orientation being may be relative to the patient's jaw bone and/or teeth.

It is an advantage to use the original shape of the tooth which the implant and the final restoration are replacing, for designing the implant, because the length, the thickness, the position and orientation of the original tooth root may be useful for the design of the implant, which to some degree may resemble or replace a tooth root. The shape of the original tooth may be derived or obtained from a scan of the tooth, such as a CT scan or a 3D surface scan of the mouth if the tooth is still present, or from an older scan of the mouth.

In some embodiments the design of the virtual implant provides that the implant is adapted to be inserted in the jaw bone of the patient with the planned implant placement, i.e. the planned implant position and orientation, being such that the implant is not placed in a tooth root from another tooth or in a nerve.

Thus the implant does not have to be inserted in a straight vertical orientation, but can inserted with a small, medium or large angle relative to vertical.

In some embodiments the method comprises virtually performing collision detection of the implant with respect to neighbor teeth roots or implants.

It is an advantage to perform a virtual test for collision detection between the planned placement of the virtual implant and neighbor teeth roots and nerves to check that there is free space for the implant when virtually planning the implant placement and e.g. also implant design. The position of the neighbor teeth roots and nerves may be determined from the obtained CT scan. The insertion can be virtually designed by e.g. starting from an initial insertion path and performing collision detection to determine whether the implant can be moved to a planned placement without collisions with the neighbor teeth. If the collision detection indicates that collisions will occur along the initial insertion path, a new path can be determined and collision tested. This continues until a suitable collision-free path is identified.

In some embodiments the method comprises virtually providing limitations for the implant relative to the visible part of the neighbor teeth.

Thus the visible part of the neighbor teeth may also impose limitations to the implant position and/or orientation and/or design. The limitation may e.g. be related a maximum acceptable angle of the longitudinal axis of the implant relative to the normal of the occlusal plane of the patient's set of teeth. It may be an advantage to define such a maximum acceptable angle relative to the occlusal plane in order to obtain a good mechanical functionality of the implant and the final restoration arranged in the implant.

In some embodiments the method comprises virtually planning the surgical drilling of the bore for the implant.

When the implant position and/or orientation has been virtually designed, then a virtual planning of the surgical drilling can be performed.

In some embodiments the method comprises virtually designing a drill guide for the boring of the implant.

When the implant position and/or orientation has been designed and/or when the virtual planning of the surgical drilling has been made, then a drill guide can be virtually designed. A drill guide may be an advantage to use for the dentist for ensuring that the implant is placed correctly in the jaw bone according to the planned placement and that the customized healing abutment fits.

In some embodiments the virtual planning of the surgical drilling and/or virtual design of the drill guide is/are designed based on the CT scan.

It is an advantage to use a CT scan for this, as teeth roots can be seen on a CT scan.

In some embodiments the virtual planning of the surgical drilling and/or virtual design of the drill guide is/are designed based on the 3D surface scan.

It is an advantage to use the 3D surface scan for this, as the visible part of the neighbor teeth can be seen and the gingival edge can be derived from this scan, which be used to advantage in the virtual planning of the surgical drilling and in the virtual design of the drill guide.

In some embodiments the method comprises virtually extracting any teeth which are placed where an implant is planned to be arranged.

It is an advantage to virtually extract teeth, so that the virtual view of the mouth looks the way it will look, more or less, as when the dentist will start physically placing the implants, because hereby the implant placement can be virtually planned, and the final restoration and customized healing abutment can be virtually designed, under conditions reflecting or corresponding to the physical conditions in the patient's mouth.

In some embodiments the method comprises virtually designing the soft tissue surrounding the customized healing abutment.

Thus the soft tissue, e.g. gingiva, around the customized healing abutment may be designed to a desired look, and the customized healing abutment may then for example be designed to fit the design of the soft tissue.

In some embodiments the method comprises virtually designing the soft tissue surrounding the customized healing abutment by using the shape of the original soft tissue from the CT scan and/or the 3D surface scan.

Thus it is an advantage to obtain a scan of the soft tissue, e.g. gingiva, around the planned implant and planned customized healing abutment, before any tooth is extracted and before the implant is placed, because the gingiva will probably look fine at this time, and the intact and undamaged gingiva can then form the basis for the design of the gingiva after the implant, customized healing abutment and/or final restoration have been placed.

In some embodiments the design of the customized healing abutment is configured for attachment of a temporary restoration to the customized healing abutment.

In some cases, e.g. if the implant and final restoration is for replacing an anterior tooth, then a temporary restoration may be attached to the customized healing abutment, because it may not be visually appealing without a front tooth for the, maybe long, period where the implant is healing.

In some embodiments the design of the customized healing abutment comprises means for attachment of a temporary restoration, such as a temporary crown or a temporary bridge.

The means for attachment may be a hole in the top of the customized abutment for example for attaching a screw retained temporary restoration. Or the temporary attachment may be attached by means of cementing or gluing the temporary restoration to the customized healing abutment.

If a temporary restoration is attached to the customized healing abutment, then the temporary restoration may be designed not to be level with the neighbor teeth but to be lower than the neighbor teeth, such that the risk of affecting the customized healing abutment with forces from collision with the antagonist or with food, is minimized.

In some embodiments the customized healing abutment comprises a screw hole for retaining the temporary restoration, such as temporary crown. This may be the case when the temporary restoration is equipped with a screw configured for engaging the screw hole.

In some embodiments the temporary restoration, such as a temporary crown, is adapted to be cemented to the customized healing abutment, such that the temporary restoration can be efficiently secured at the customized healing abutment until the implant has healed to the jaw bone.

In some embodiments the method comprises virtually designing a temporary restoration for attachment to the customized healing abutment.

The temporary restoration may comprise a stock abutment and a crown, or a screw retained crown, or a two-piece restoration comprising a coping and a crown on the customized healing abutment, or a one-piece restoration comprising a crown on the customized healing abutment.

For the stock abutment, the customized healing abutment may be the stock abutment.

The parts or components of the temporary restoration, e.g. coping etc, may also be customized because the customized healing abutment is unique, so the other components attached to it could or should also be customized for fitting and matching the customized healing abutment.

The CT scan and/or the 3D surface scan capture at least part of the patient's mandibular or maxillary or at least a part of both.

In some embodiments the CT scan is a cone-beam CT scan (CBCT scan).

In some embodiments the 3D surface scan is an intra oral scan captured directly in the patient's mouth, and/or a scan of a physical impression of the patient's teeth/gums, and/or a scan of a physical model of the patient's teeth/gums.

Note, that in this application we describe scanning the teeth and the customized healing abutment attached to the implant. The scanning may be performed by means of CT scanning. However, it may also be an advantage to perform the scanning by 3D intra oral scanning directly in the mouth of the patient using an intra oral scanner. However, instead of direct intra oral scanning, an impression of the patient's teeth and/or the customized healing abutment arranged in the implant may be obtained, and the customized healing abutment in the impression may then be an analog. The impression may be scanned in a 3D desktop scanner suitable for scanning impressions. However, a physical model of the teeth may be performed by casting the model from the impression, and the physical model may then be scanned in a 3D desktop scanner suitable for scanning teeth models.

The intra-oral scanner may be configured for utilizing focus scanning, where the digital 3D representation of the scanned teeth is reconstructed from in-focus images acquired at different focus depths. The focus scanning technique can be performed by generating a probe light and transmitting this probe light towards the set of teeth such that at least a part of the set of teeth is illuminated. Light returning from the set of teeth is transmitted towards a camera and imaged onto an image sensor in the camera by means of an optical system, where the image sensor/camera comprises an array of sensor elements. The position of the focus plane on/relative to the set of teeth is varied by means of focusing optics while images are obtained from/by means of said array of sensor elements. Based on the images, the in-focus position(s) of each of a plurality of the sensor elements or each of a plurality of groups of the sensor elements may be determined for a sequence of focus plane positions.

The in-focus position can e.g. be calculated by determining the light oscillation amplitude for each of a plurality of the sensor elements or each of a plurality of groups of the sensor elements for a range of focus planes. From the in-focus positions, the digital 3D representation of the set of teeth can be derived.

Obtaining a three dimensional representation of the surface of an object by scanning the object in for example a 3D desktop scanner can be denoted 3D modeling, which is the process of developing a mathematical representation of the three-dimensional surface of the object via specialized software. The product is called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner describes the distance to a surface at each point in the picture.

For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time.

An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

In some embodiments the method comprises virtually designing a radiographic template adapted for placement on the patient's teeth to simulate the implant position and/or the final restoration.

In some embodiments the method comprises obtaining a CT scan and/or a 3D surface scan of a radiographic template arranged on the patient's teeth. It is an advantage to design a radiographic template to be placed on the patient's teeth, such as in the mouth of the patient, because when scanning the teeth and the template, the design of the final restoration can be translated to or used or seen in connection with the patient's existing teeth. Where there are no teeth, the radiographic template may lie directly on the jaw in the patient's mouth. Instead of intra oral scanning, an impression or a physical model of the patient's teeth may be produced and scanned. The radiographic template may contain a material which can be captured specifically by a CT scan, such as barium.

In some embodiments, at least one of the steps of the method is computer-implemented.

In some embodiments, the virtually placing the implant and virtually designing the customized healing abutment are performed as part of an iterative process where each iteration of the iterative process comprises evaluating the implant placement and/or the customized healing abutment design and based on a result of the evaluation determining whether the implant placement and/or the customized healing abutment design must be modified. The evaluation of the implant placement can be with respect to support provided by the patient's jaw bone, i.e. how much bone material is available to hold the implant and whether the jaw bone is healthy. The evaluation of the implant placement can also be with respect to whether it is possible to drill the bore into the patient's jaw bone at the planned implant placement. Neighbor teeth may be obstructing such that there is not sufficient space for the dentist to arrange the surgical drilling tool at an appropriate position relative to the patient's teeth and jaw bone. The evaluation of the implant placement can also be with respect to the expected mechanical robustness of the implant when arranged in the patient's jaw bone. A large offset from the normal to the occlusal plane may e.g. introduce problems due to the forces applied to the implant during mastication.

In some embodiments, the evaluation of the iterative process takes into account the design of the final restoration.

When arranged in the patient's jaw bone the implant will ultimately form the support for the final restoration, e.g. via an implant abutment, and it is thus advantageous to ensure that the planned implant placement is adequate for supporting the final restoration. The customized healing abutment preferably shapes the soft tissue according to a target profile that fits the final restoration. It is thus an advantage to take the design of the final restoration into account when evaluating the customized healing abutment design.

In some embodiments, the virtually designing the final restoration is part of the iterative process and where the evaluation determines whether the design of the final restoration must be modified.

This provides the advantage that the dentist can determine whether a current design of the final restoration will put undesired limitations on the design of the customized healing abutment and on the planned implant placement. For instance a current design of the final restoration may require a very high precision in e.g. the implant placement such that problems occur if deviations in the implant placement are introduced by the surgical drilling or the osseointegration. A current design of the final restoration may also limits the range of possible designs of the customized healing abutment unnecessarily.

In some embodiments, the implant placement is modified based on the designed customized healing abutment and/or based on the designed final restoration.

In some cases some adjustment in the implant placement is acceptable while the dentist prefers to maintain a chosen design of the final restoration, e.g. if the design fits the shape of an extracted tooth. Likewise, the dentist may have a preferred shape of the customized healing abutment and wishes to maintain that shape while being prepared to accept some modification of the implant placement.

In some embodiments, the customized healing abutment is redesigned based on the modified implant placement and/or based on the designed final restoration.

In some cases some adjustment in the design of the customized healing abutment is acceptable and the dentist prefers to maintain a chosen design of the final restoration. Likewise, the dentist may have a preferred implant placement after having consulted the CT scan and wishes to maintain that placement while being willing to allow some modification to the design of the customized healing abutment.

In some embodiments, the iterative process comprises redesigning the final restoration based on the modified implant placement and/or on the redesigned customized healing abutment.

Redesigning the final restoration may have the advantage that it is much easier to obtain the planned implant placement in the patient's jaw bone and that the redesigned customized healing abutment is much easier to manufacture.

In some embodiments, the drill guide is virtually designed based on the planned implant placement after the last iteration of the iterative process. This may ensure that when the dentist uses the drill guide while surgically drilling the bore into the patient's jaw bone, the bore is at an optimal position and orientation relative to the planned implant placement.

The present invention relates to different aspects including the method described above and in the following, and corresponding methods, devices, apparatuses, systems, products, uses, kits and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a method of virtually planning and designing an implant procedure for a patient, where the method comprises designing a customized healing abutment for the implant and a drill guide for the surgical drilling of a bore for the implant into the patient's jaw bone, where the method comprises:
  obtaining a CT scan of at least part of a patient's mouth;
  virtually placing one or more implants adapted for replacing at least part of the not visible part of the one or more original teeth, such that a planned implant placement is defined;
  virtually designing one or more customized healing abutments adapted for insertion into the one or more implants and for shaping the surrounding soft tissue according to a target profile;
  virtually designing a drill guide adapted for surgical drilling of bores for the implants into the bone of the patient through the drill guide, where the drill guide is designed to ensure that the bores are such that the implants placed in the bores are arranged according to the planned implant placement and the customized healing abutments can shape the soft tissue according to the target profile when arranged in the implant.

In some embodiments, the method comprises virtually providing guide limitations for placement of the implants and/or virtually testing for and providing warnings for collision of implants with other implants or teeth roots.

In some embodiments, the method comprises virtually placing one or more final restorations adapted for replacing the visible part of one or more original teeth, where the original teeth are adapted to be extracted.

In particular, disclosed herein is a method of virtually planning and designing an implant procedure for a patient, where the method comprises designing a drill guide and a customized healing abutment for the implant, where the method comprises:
  obtaining a 3D surface scan of at least part of a patient's mouth;
  obtaining a CT scan of at least part of a patient's mouth;
  virtually aligning the 3D surface scan and the CT scan;
  virtually placing one or more final restorations adapted for replacing the visible part of one or more original teeth, where the original teeth are adapted to be extracted;
  virtually placing one or more implants adapted for replacing at least part of the not visible part of the one or more original teeth;
  virtually providing guide limitations for placement of the implants;
  virtually testing for and providing warnings for collision of implants with other implants or teeth roots;
  virtually designing one or more customized healing abutments adapted for insertion into the one or more implants;
  virtually designing one or more final implant abutments adapted for insertion into the one or more implants;
  virtually designing the one or more virtually placed final restorations adapted for attachment to the one or more final implant abutments.
  virtually designing a drill guide adapted for drilling bores for the implants into the bone of the patient through the drill guide.

The visible part of the original teeth can be replaced by the final restorations in the CT scan by virtually aligning the final restorations with the CT scan. Optionally the CT scan is also aligned with a 3D surface scan to provide more information relating to e.g. the soft tissue and the surface of the teeth.

In particular, disclosed herein is a method of manufacturing a drill guide, where the drill guide is virtually designed using the method according to any one of the embodiments.

For example the virtual design of the drill guide can be designed based on the CT scan, and/or the virtual design of the drill guide can be designed based on a 3D surface scan.

In particular, disclosed herein is a method of manufacturing a customized healing abutment, where the customized healing abutment is virtually designed using the method according to any one of the embodiments.

In particular, disclosed herein is a system for virtually designing a customized healing abutment and a drill guide for a patient, where the system comprises:
  means for obtaining a CT scan comprising at least part of the patient's jaw bone;
  means for virtually placing at least one implant relative to the jaw bone of the CT scan such that a planned implant placement is defined;
  means for virtually designing:
    a drill guide for guiding the surgical drilling of a bore for the implant into the patient's jaw bone at the planned implant placement; and
    a customized healing abutment configured for shaping the soft tissue according to a target profile when arranged in the implant,
  where the design of the drill guide and of the customized healing abutment is at least partly based on the CT scan and on the planned implant placement.

In particular, disclosed herein is a system for virtually designing a customized healing abutment for a patient, where the system comprises:
  means for obtaining a CT scan comprising at least part of the patient's teeth including teeth roots;
  means for virtually placing at least one implant relative to the teeth of the CT scan, where the physical implant is adapted for replacing an original tooth root in the jaw bone of the patient;
  means for virtually designing a customized healing abutment, where the physical customized healing abutment is adapted for insertion into the implant for allowing soft tissue at the implant to heal properly before attachment of a final restoration in the implant, and where the design of the customized healing abutment is at least partly based on the CT scan and on the virtual implant placement.

The means for may be processing means in a computer, such as a processor.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

In some embodiments, the system comprises a non-transitory computer readable medium having one or more computer instructions stored thereon, where said computer instructions comprises instructions for carrying out a method of virtually designing a customized healing abutment and a drill guide for a patient, where the method comprises:
  obtaining a CT scan comprising at least part of the patient's jaw bone;
  virtually placing at least one implant relative to the jaw bone of the CT scan, such that a planned implant placement is defined;
  virtually designing
    a drill guide for guiding the surgical drilling of a bore for the implant into the patient's jaw bone at the planned implant placement; and
    a customized healing abutment configured for shaping the soft tissue according to a target profile when arranged in the implant,
  where the design of the drill guide and of the customized healing abutment is at least partly based on the CT scan and on the planned implant placement.

Disclosed is a non-transitory computer readable medium storing thereon a computer program, where said computer program is configured for causing a computer-assisted method of virtually designing a customized healing abutment for a patient, where the method comprises:
  obtaining a CT scan comprising at least part of the patient's teeth including teeth roots;

virtually placing at least one implant relative to the teeth of the CT scan, where the physical implant is adapted for replacing an original tooth root in the jaw bone of the patient;

virtually designing a customized healing abutment, where the physical customized healing abutment is adapted for insertion into the implant for allowing soft tissue at the implant to heal properly before attachment of a final restoration in the implant, and where the design of the customized healing abutment is at least partly based on the CT scan and on the virtual implant placement.

Disclosed is a non-transitory computer readable medium storing thereon a computer program, where said computer program is configured for causing a computer-assisted method of virtually designing a customized healing abutment and a drill guide for a patient, where the method comprises:

obtaining a CT scan comprising at least part of the patient's jaw bone;

virtually placing at least one implant relative to the jaw bone of the CT scan such that a planned implant placement is defined;

virtually designing:
  a drill guide for guiding the surgical drilling of a bore for the implant into the patient's jaw bone at the planned implant placement; and
  a customized healing abutment configured for shaping the soft tissue according to a target profile when arranged in the implant where the design of the drill guide and the customized healing abutment is at least partly based on the CT scan and on the planned implant placement.

Disclosed is a user interface for virtually designing a customized healing abutment and a drill guide for a patient, where the user interface is configured for:

obtaining and visualizing a CT scan comprising at least part of the patient's jaw bone;

virtually placing at least one implant relative to the jaw bone of the CT scan such that a planned implant placement is defined; and virtually designing:
  a drill guide for guiding the surgical drilling of a bore for the implant into the patient's jaw bone at the planned implant placement; and
  a customized healing abutment configured for shaping the soft tissue according to a target profile when arranged in the implant where the design of the drill guide and the customized healing abutment is at least partly based on the CT scan and on the planned implant placement.

In some embodiments, the user interface is configured for obtaining and visualizing a 3D surface scan comprising at least part of the teeth and soft tissue of the patient's mouth.

In some embodiments, the user interface is configured for performing an alignment of the CT scan and the 3D surface scan before designing the customized healing abutment and the drill guide.

In some embodiments, the user interface is configured for virtually placing a final restoration for the implant relative to the CT scan and/or relative to the 3D surface scan, and for virtually designing the final restoration. In the patient's mouth the final restoration can be connected to the implant via an implant abutment. In the user interface, it is not necessary to visualize such an implant abutment.

In some embodiments, the user interface is configured for virtually placing the final restoration before virtually placing the implant.

In some embodiments, the user interface is configured for being visualized to an operator using a computer screen and for allowing the operator to enter data into and to make choices presented in the user interface by means of a computer keyboard or a computer mouse.

In some embodiments, the user interface is configured for visualizing the implant together with the CT scan and optionally the 3D surface scan, and the user interface comprises a virtual tool for performing designing of the customized healing abutment and the drill guide when activated.

Disclosed is a kit comprising a customized healing abutment and a drill guide for a patient, where the kit comprises:

a drill guide for guiding the surgical drilling of a bore for the implant into the patient's jaw bone at the planned implant placement; and a customized healing abutment configured for shaping the soft tissue according to a target profile when arranged in the implant where the drill guide and of the customized healing abutment are configured to provide that an implant arranged in a bore drilled using the drill guide is placed at the planned implant placement such that the customized healing abutment can shape the soft tissue according to the target profile when arranged in the implant.

Disclosed is a method of virtually designing a customized healing abutment for a patient, where the method comprises:

obtaining a CT scan comprising at least part of the patient's jaw bone;

obtaining information relating to an implant screw by which the customized healing abutment is to be attached to an implant, where the implant screw comprises a screw head; and virtually designing a customized healing abutment taking into account the implant screw information, where an uppermost surface of the customized healing abutment is designed to comprise an opening for accommodating the screw head, and where the customized healing abutment is designed to provide a smooth transition from the customized healing abutment to the implant screw.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 14 shows an example of a manufactured drill guide for drilling holes for implants in a patient's jaw.

FIG. 15 shows an example of a customized healing abutment with scan markers.

FIG. 20 shows a design of the customized healing abutment where the transition to the implant screw is smooth.

DETAILED DESCRIPTION

In the following description, reference is made to the accompanying figures, which show by way of illustration how the invention may be practiced.

FIG. 18 shows a schematic of a procedure for replacing a tooth with a dental restoration and an implant.

Figure 18A:
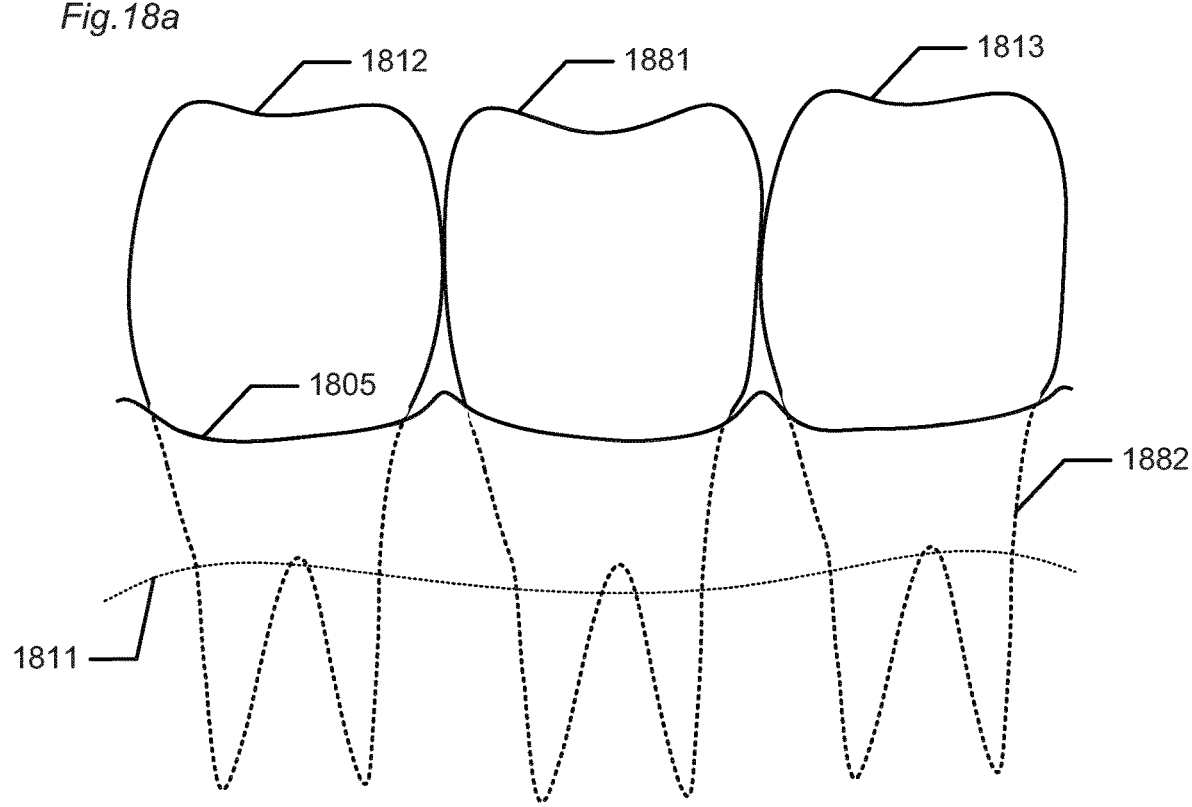
FIG. 18 shows a schematic of a procedure for replacing a tooth with a dental restoration and an implant.

FIG. 18a shows three of the patient's teeth 1812, 1813, 1881 where the tooth 1881 in the middle is to be extracted and replaced by an implant and a final restoration, e.g. because the tooth is dead and has become fragile. Sub-gingivally, i.e. below the surface of the gingiva 1805, the teeth have cervical portions 1882 which engage the patient's jaw bone 1811 such that the teeth are held firmly in the patient's mouth. The dotted lines in the Figure represent sub-gingival elements.

Figure 18B:
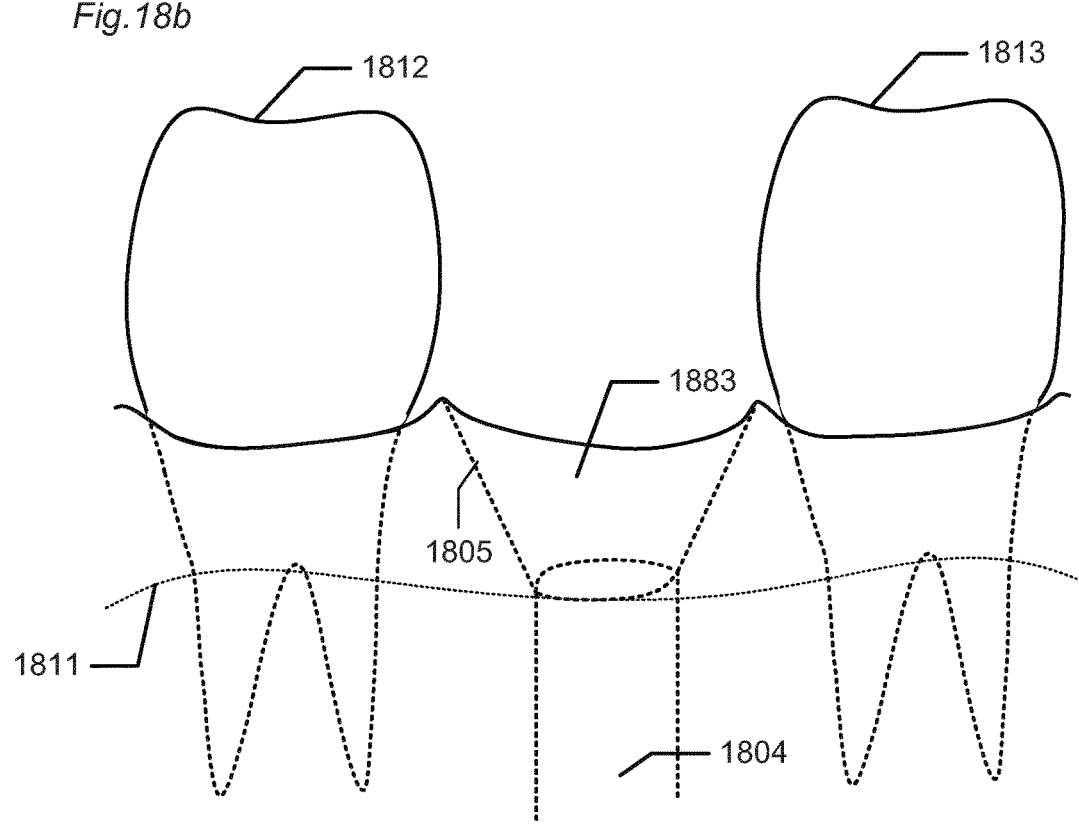
Figure 18C:
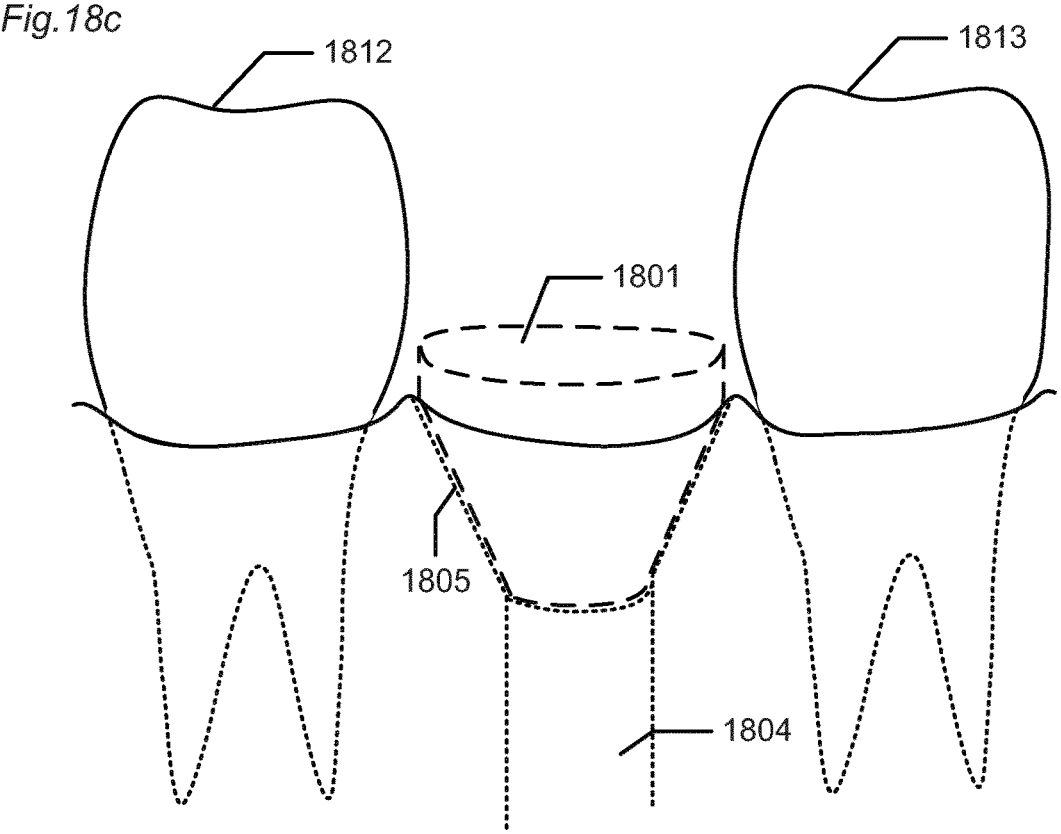

Immediately after the tooth 1881 is extracted the space which previous was occupied by the extracted tooth 1881 forms a hole 1883 in the gingiva 1805 between the teeth 1812, 1813. A bore is drilled into the jaw bone 1811 at this hole 1883 and an implant 1804 is arranged in the bore as illustrated in FIG. 18b.

In order to prevent the soft tissue from collapsing into the hole 1883, a healing abutment 1801 is connected to the implant 1804 such that the outer surface of the healing abutment 1801 can act as a support for the gingiva 1805 during the osseointegration of the implant 1804 into the jaw bone. The healing abutment 1801 illustrated in FIG. 18c has a flat uppermost surface but other geometries are also acceptable and the surface may have an opening for an implant screw.

Figure 18D:
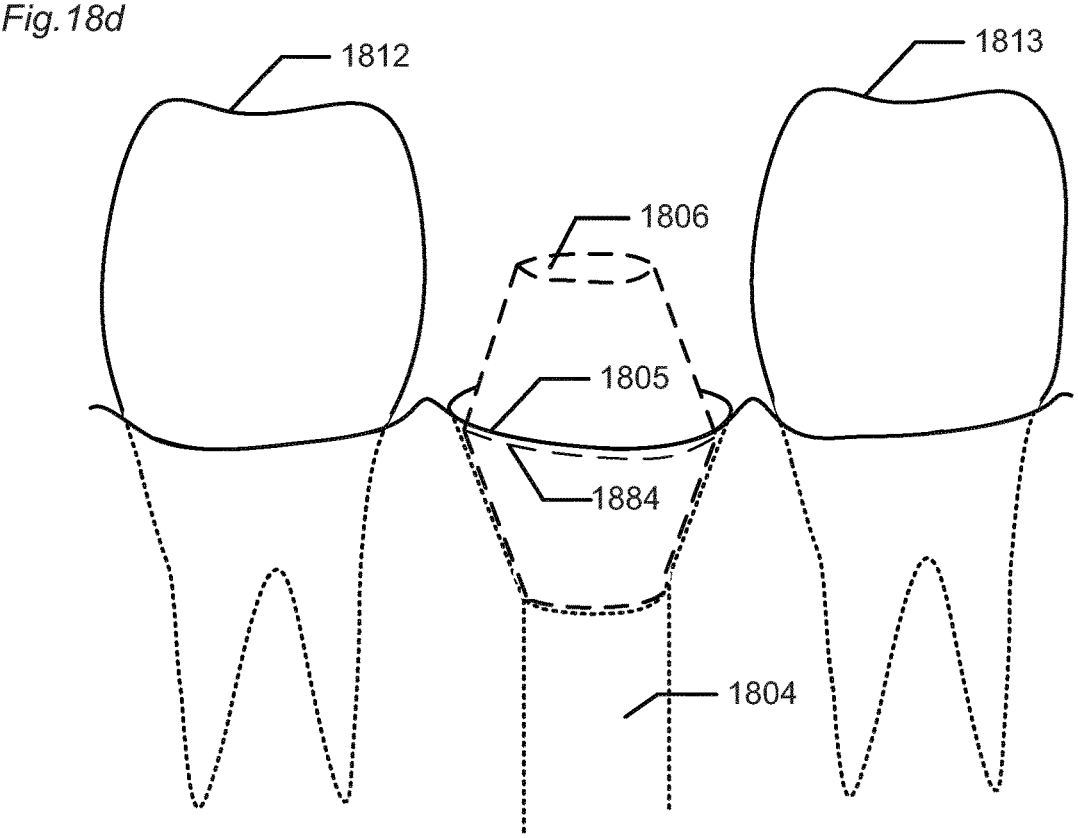

When the osseointegration is completed the healing abutment is removed and replaced by an implant abutment 1806 configured for supporting a final restoration as illustrated in FIG. 18d. The implant abutment is here designed to have a margin line 1884 just below the surface of the gingiva 1805.

Figure 18E:
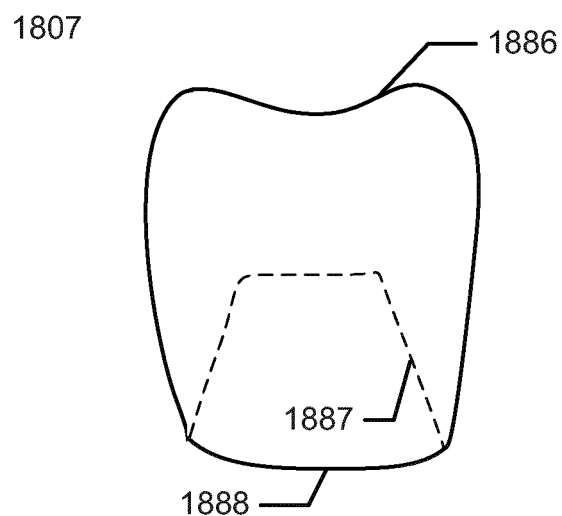

FIG. 18e shows the final restoration 1807 designed to be arranged at the implant abutment. The final restoration 1807 has an outer surface 1886 which is shaped according to a desired anatomical shape of the tooth, such as the shape of the original tooth if the patient was happy with this shape, and an abutment engaging surface 1887 shaped to allow the final restoration to be arranged at the implant abutment. The margin line 1888 of the tooth is designed to fit the margin line of the implant abutment.

Figure 18F:
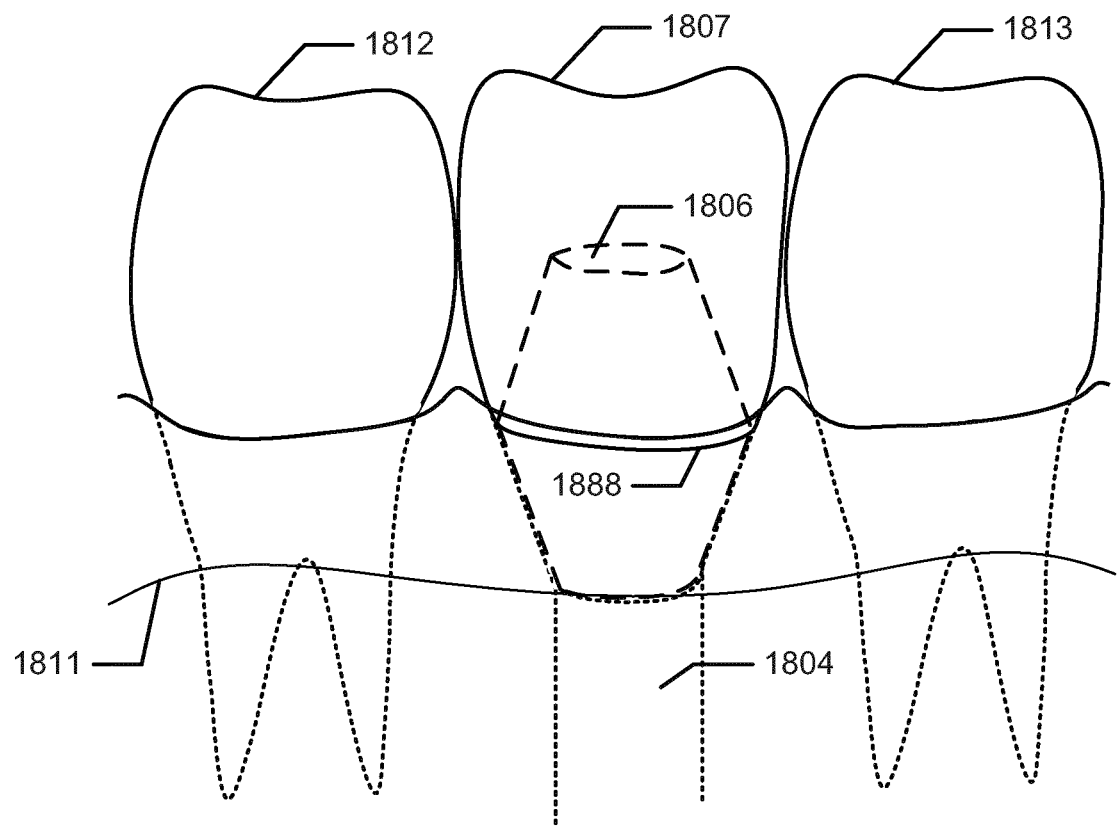

FIG. 18f illustrates the patient's teeth with the extracted tooth replaced by the final restoration 1807 arranged at the implant 1804 via the implant abutment 1806. The implant is secured in the jaw bone 1811 such that the final restoration 1807 is firmly fixated in the patient's mouth. The final restoration 1807 is shaped to provide an aesthetic appearance together with the surrounding teeth 1812, 1813.

FIG. 1a shows a flowchart of the method of virtually designing a customized healing abutment for a patient.

In step 101a a CT scan comprising at least part of the patient's jaw bone and teeth including teeth roots is obtained.

In step 102a at least one implant is virtually placed relative to the jaw bone and the teeth of the CT scan. The virtual implant corresponds to a physical implant, where the physical implant is adapted for replacing an original tooth root in the jaw bone of the patient.

In step 103a a customized healing abutment is virtually designed. A physical customized healing abutment can be manufactured from the virtual customized healing abutment corresponds, where the physical customized healing abutment is adapted for insertion into the implant for allowing soft tissue at the implant to heal properly before attachment of a final restoration in the implant. The design of the customized healing abutment is at least partly based on the CT scan and on the virtual implant placement.

A step of virtually placing a final restoration for the implant relative to the jaw bone of the CT scan can be performed before the step 102a of virtually placing the implant, such that the placement of the implant takes into account a desired shape and placement of the final restoration.

Figure 1B:
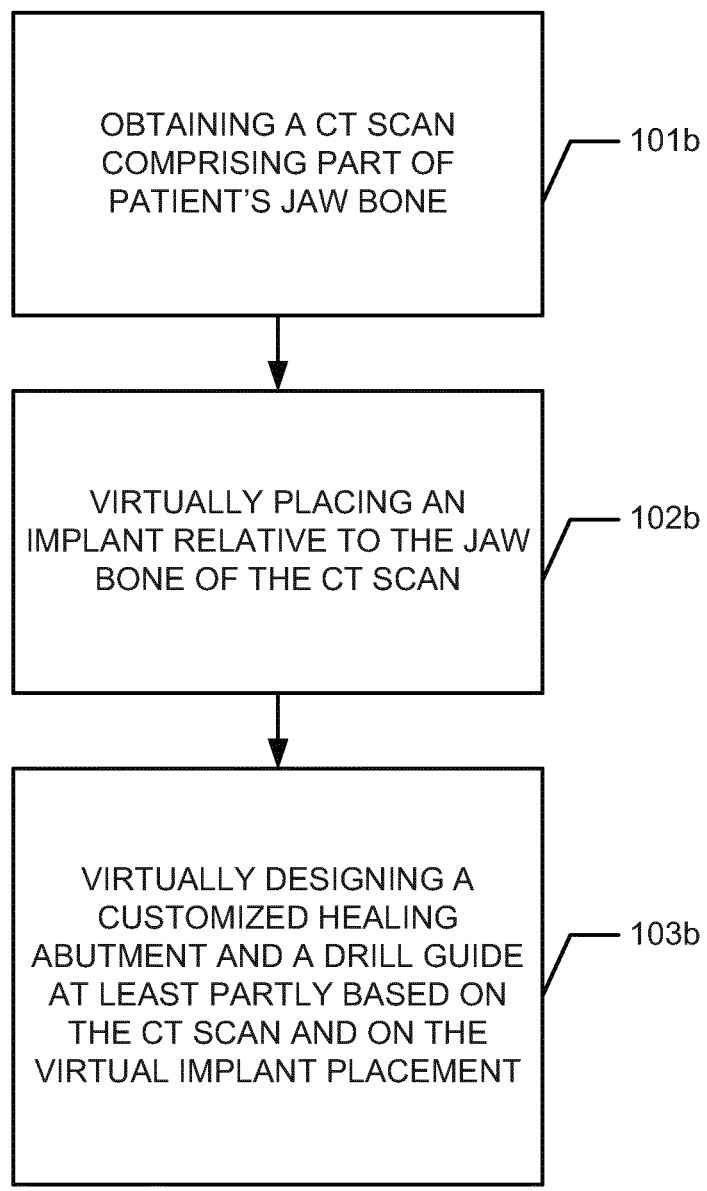
FIG. 1 shows a flowchart of a method of virtually designing a customized healing abutment for a patient.

FIG. 1b a flowchart of the method of virtually designing a customized healing abutment and a drill guide for a patient.

In step 101b, a CT scan comprising at least part of the patient's jaw bone is obtained.

In step 102b, at least one implant is virtually placed relative to the jaw bone in the CT scan such that a planned implant placement is defined.

In step 103b is virtually designed:
  a drill guide for guiding the surgical drilling of a bore for the implant into the patient's jaw bone at the planned implant placement; and
  a customized healing abutment configured for shaping the soft tissue according to a target profile when arranged in the implant;

The design of the drill guide and of the customized healing abutment is at least partly based on the CT scan and on the planned implant placement.

Figure 2:
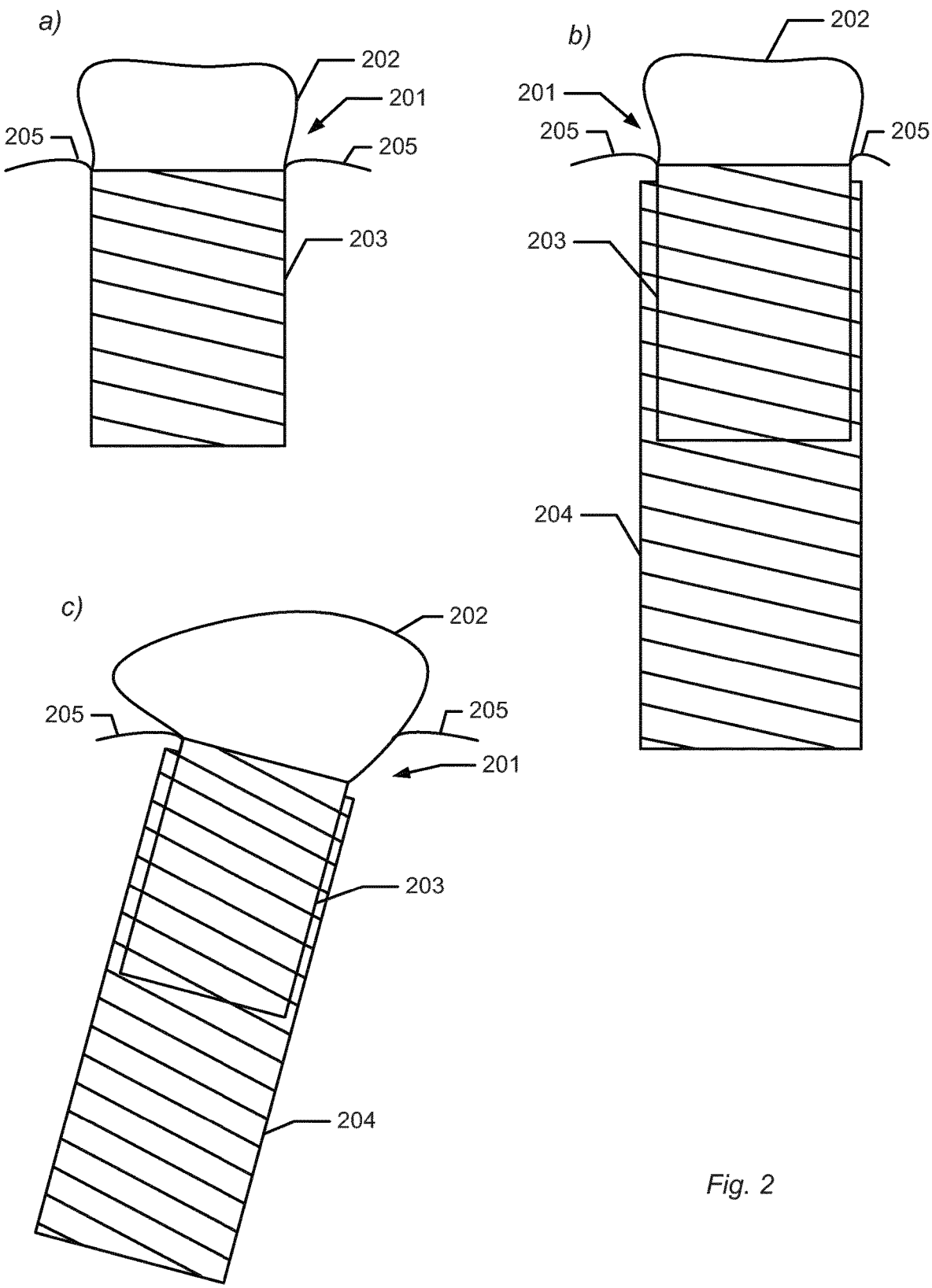
FIG. 2 shows schematic examples of customized healing abutments.

FIG. 2 shows schematic examples of customized healing abutments.

FIG. 2a) shows an example of a customized healing abutment 201 comprising a top part 202 and a screw part 203. The top part 202 is the part configured for emerging from the implant edge through the soft tissue and potentially passes through the gingiva to be visible above the gingiva next to the neighboring teeth. The position of the gingiva 205 is indicated.

FIG. 2b) shows an example of a customized healing abutment 201 arranged in an implant 204. The screw part 203 of the customized healing abutment is screwed into the implant 203. The top part 202 protrudes from the implant 204.

FIG. 2c) shows an example of a customized healing abutment 201 arranged in an implant 204, where the implant is arranged in the jaw bone of the patient with a skew angle relative to vertical, where horizontal or normal is indicated by the gingiva 205. The screw part 203 and the top part 202 of the customized healing abutment 201 have the boundary relative to each other perpendicular to the longitudinal axis of the implant. However the boundary between the top part and the screw part of the customized healing abutment may alternatively be level with the gingiva, or somewhere in between being level with the gingiva and being perpendicular to the longitudinal axis of the implant. The screw part of the customized healing abutment should however just be able to be screwed down into the implant.

In FIGS. 2a) and 2b) the boundary between the top part and the screw part of the customized healing abutment is indicated to be level with the gingiva, but it is understood that the customized healing abutment and gingiva may be in contact anywhere along the customized healing abutment.

In FIG. 2c) the contact between the customized healing abutment and the gingiva is at the boundary between the top part and the screw part of the customized healing abutment at the point to the left in the figure. However at the point to the right in the figure the contact between the customized healing abutment and the gingiva is almost at half the height of the top part of the customized healing abutment. This is due to the skew angle of the implant relative to the level of the gingiva.

Figure 3:
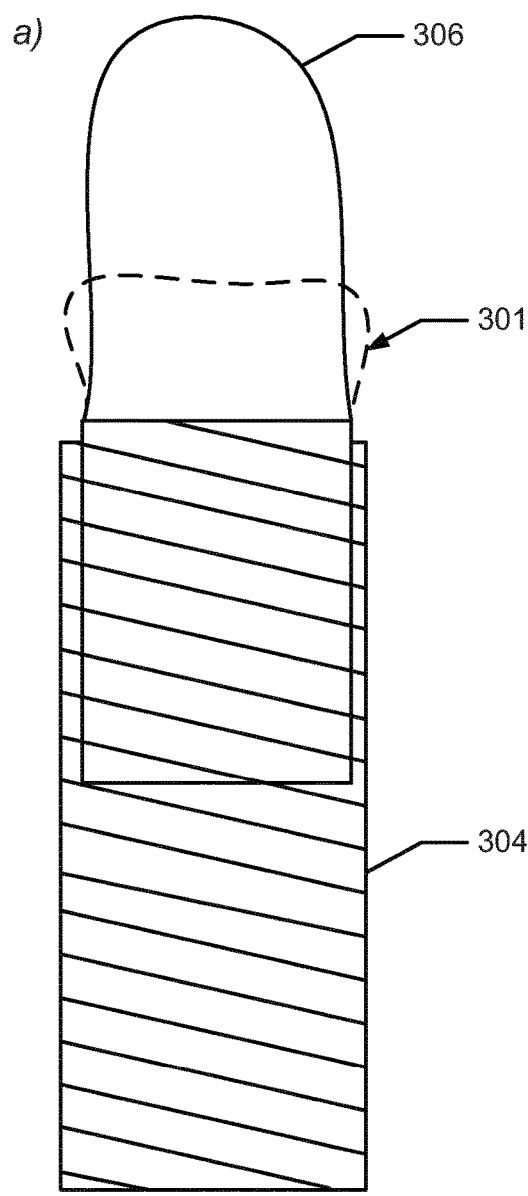
FIG. 3 shows schematic examples of an implant abutment and a final restoration in an implant.
Figure 3:
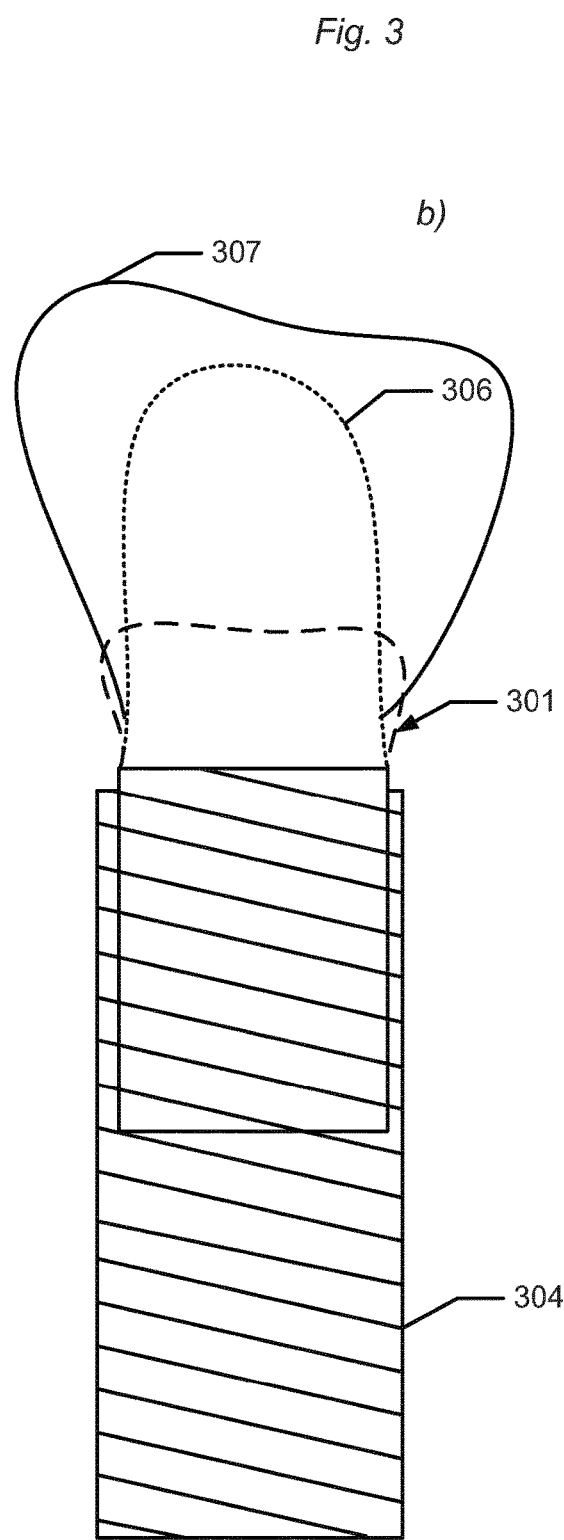

FIG. 3 shows schematic examples of an implant abutment, a customized healing abutment and a final restoration in an implant.

FIG. 3a) shows an example of a customized healing abutment 301 in dotted lines in an implant 304 similar to the customized healing abutment in FIGS. 2a) and 2b). The implant abutment 306 for a final restoration is also shown. The customized healing abutment 301 and the implant abutment 306 are not configured for being arranged in the implant 304 at the same time. The customized healing abutment is configured to be arranged in the implant while the implant connects to the jaw bone through osseointegration. When healing is complete, i.e. the implant is firmly connected to the jaw bone, the customized healing abutment is removed from the implant, and the implant abutment can be arranged in the implant instead.

FIG. 3b) shows an example of a final restoration 307 for the implant abutment 306 in the implant 304, where the implant abutment 306 and the final restoration 307 are configured for being arranged in the implant 306 after healing with the customized healing abutment 301. The customized healing abutment 301 is shown in dotted lines to indicate that it is not present simultaneously with the implant abutment 306 and the final restoration 307. It is understood that the dimensions of the customized healing abutment, the implant abutment and the final restoration may be different than shown in these figures, for example the customized healing abutment may be bigger or small or wider or narrower relative to the implant abutment and to the final restoration than shown in the figure. The customized healing abutment preferably shapes and/or maintains the shape of the gingiva for the insertion of the final restoration.

Figure 4:
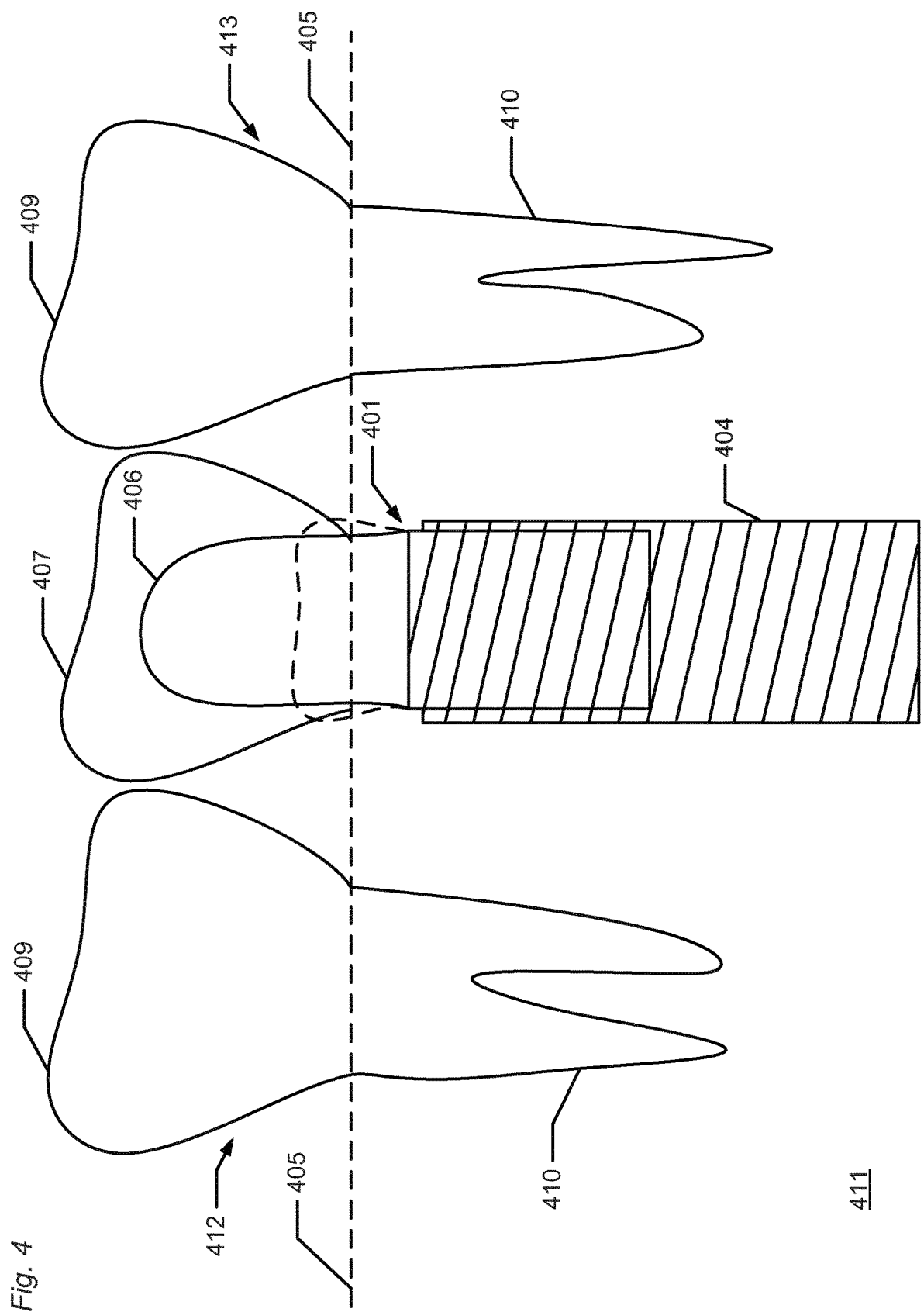
FIG. 4 shows a schematic example of an implant with a final restoration in the jaw of a patient.

FIG. 4 shows a schematic example of an implant with a final restoration in the jaw of a patient.

FIG. 4 shows an implant 404 in the jaw bone 411 of a patient. A final restoration 407 is attached to the implant 404 through an implant abutment 406. The implant abutment 406 may be customized like the healing abutment 401. The customized healing abutment 401 is also shown, even though it will not be present in the implant 404 at the same time as the implant abutment 406 and the final restoration.

In the jaw bone 411 next to the implant 404 original teeth 412 and 413 are present. Original teeth 412 and 413 comprises a natural crown 409 and natural roots 410. The gingiva 405 is shown to be present at the edge between the roots 410 and the crown 409, however it is understood that the gingiva may be present anywhere lower or higher on the tooth 412, 413.

FIG. 5 shows schematic examples of final restorations for an implant.

Figure 5B:
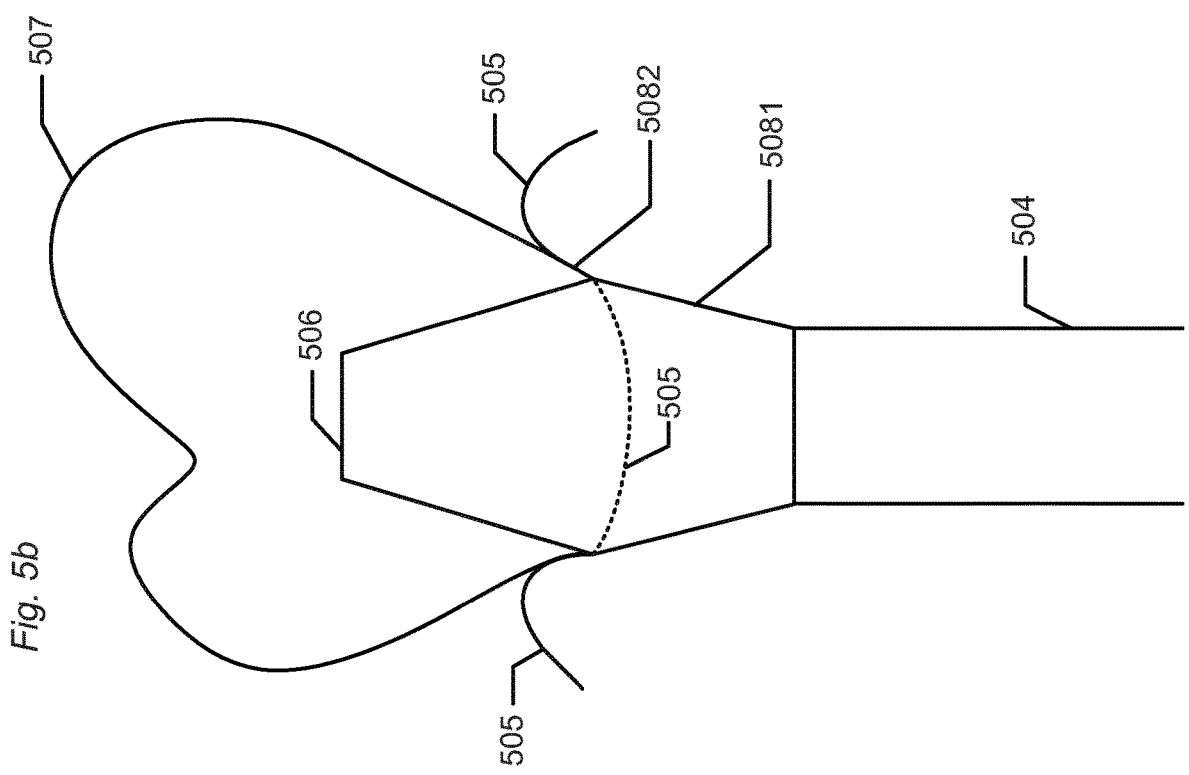
FIG. 5 shows schematic examples of final restorations for implant.
Figure 5A:
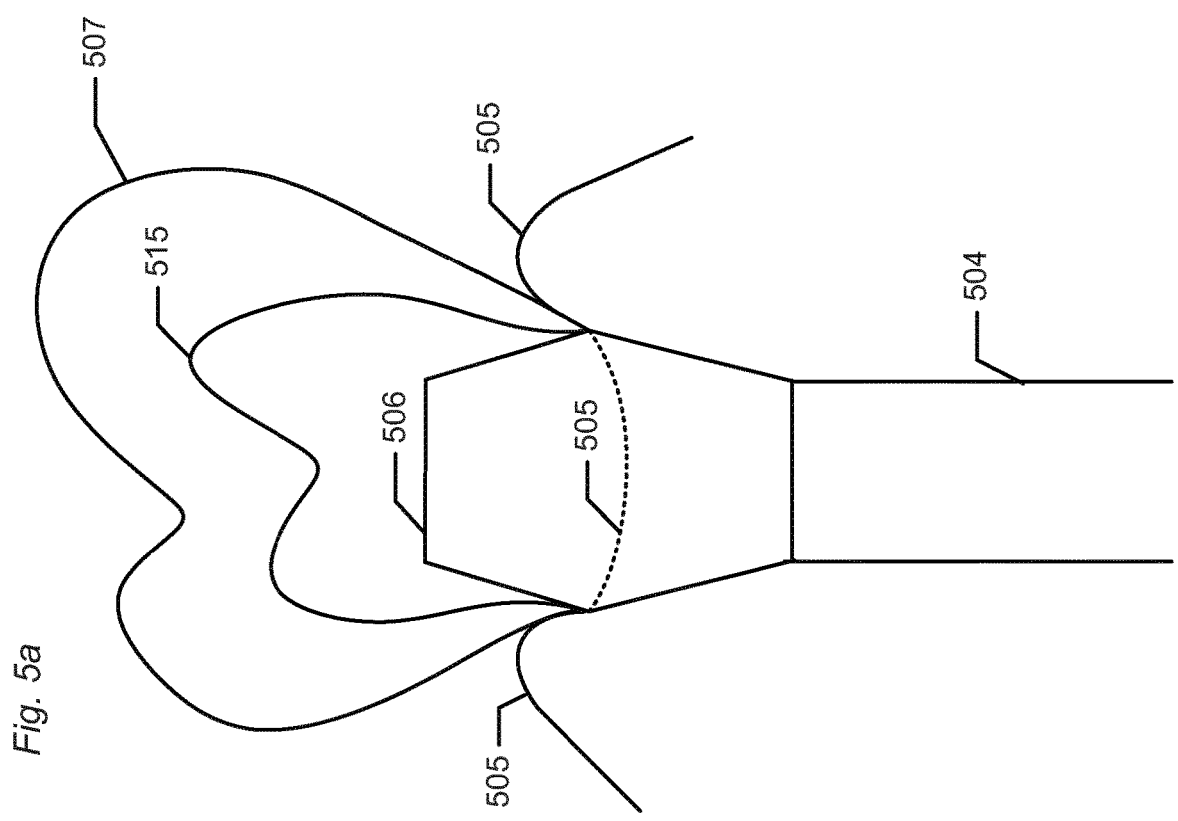

FIG. 5a) shows an example of a final restoration 507 for an implant 504, where the final restoration is arranged on a coping 515 on a standard implant abutment 506. The coping may be customized. The final restoration 507 may be or may comprise a veneering layer. Gingiva is indicated by reference number 505.

FIG. 5b) shows an example where the final restoration 507 is arranged on a standard implant abutment 506 secured in an implant 504 arranged in a bore drilled into the patient's jaw bone. The emergence profile 5081 of the abutment 506 is the axial contour of the abutment 506 where it rises from the implant 506, i.e. from the implant towards the gingiva-air interface. The emergence profile 5082 of the restoration 506 is the axial contour of the restoration where it emerges from the gingiva 505.

FIG. 5c) shows an example where the final restoration is arranged on a screw retained 516 implant abutment 506.

FIG. 5d) shows an example where the final restoration 507 is arranged on a different type of screw retained 516 implant abutment 506.

Figure 6:
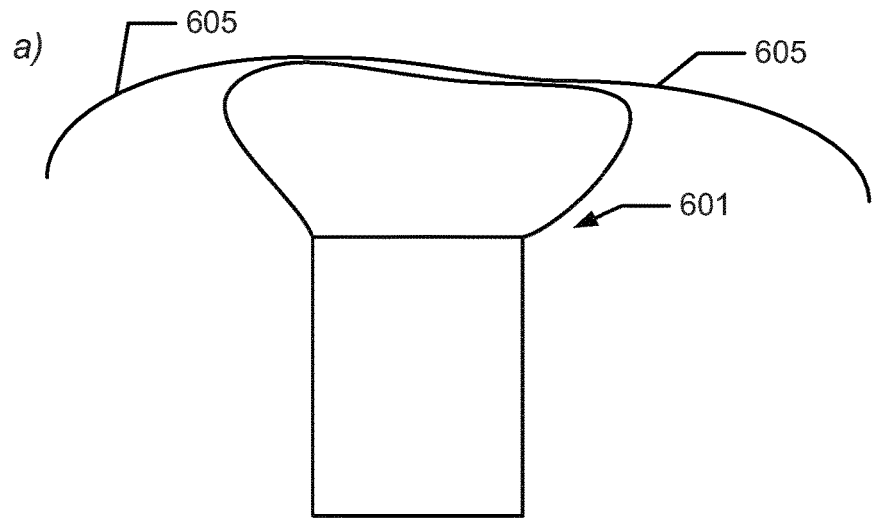
FIG. 6 shows schematic examples of different relations of a customized healing abutment relative to the gingiva.
Figure 6:
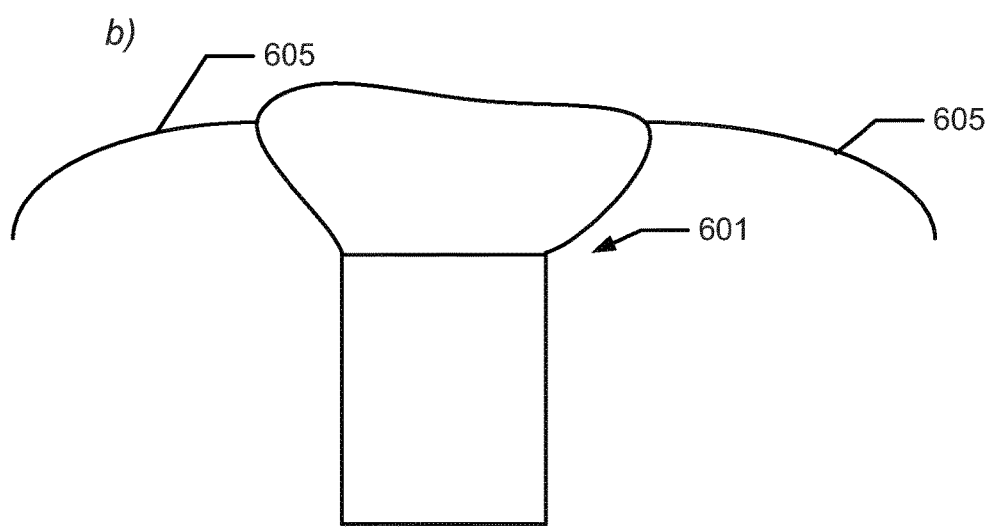
Figure 6:
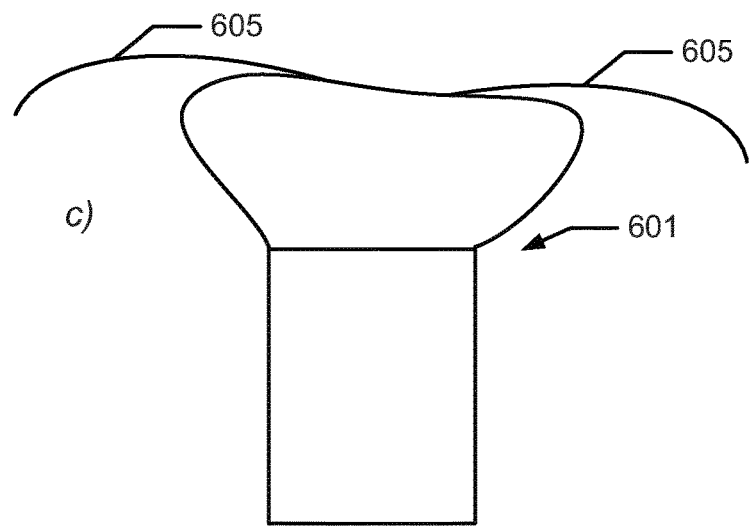

FIG. 6 shows schematic examples of different relations of the customized healing abutment relative to the gingiva.

In FIG. 6a) the customized healing abutment 601 is arranged relative to the gingiva 605 such that the customized healing abutment 601 cannot be seen, i.e. the gingiva 605 just covers the customized healing abutment 601.

In FIG. 6b) the customized healing abutment 601 is arranged relative to the gingiva 605 such that the customized healing abutment 601 is visible, i.e. the gingiva 605 do not cover the upper surface of the customized healing abutment 601.

In FIG. 6c) the customized healing abutment 601 is arranged relative to the gingiva 605 such that the customized healing abutment 601 is partly visible, i.e. the gingiva 605 covers some but not the entire upper surface of the customized healing abutment 601.

The percentage or amount or part of coverage of the upper surface of the customized healing abutment by the gingiva can be any value. I.e. the gingiva can be for example 5 mm, 4 mm, 3 mm, 2 mm, 1 mm above or below the upper surface of the customized healing abutment. It is understood that the value need not be an integer of mm but can be any integer or decimal number, e.g. 1.8 mm, 2.1 mm, 3.4 mm, 4.5 mm, 5.2 mm etc.

Figure 7:
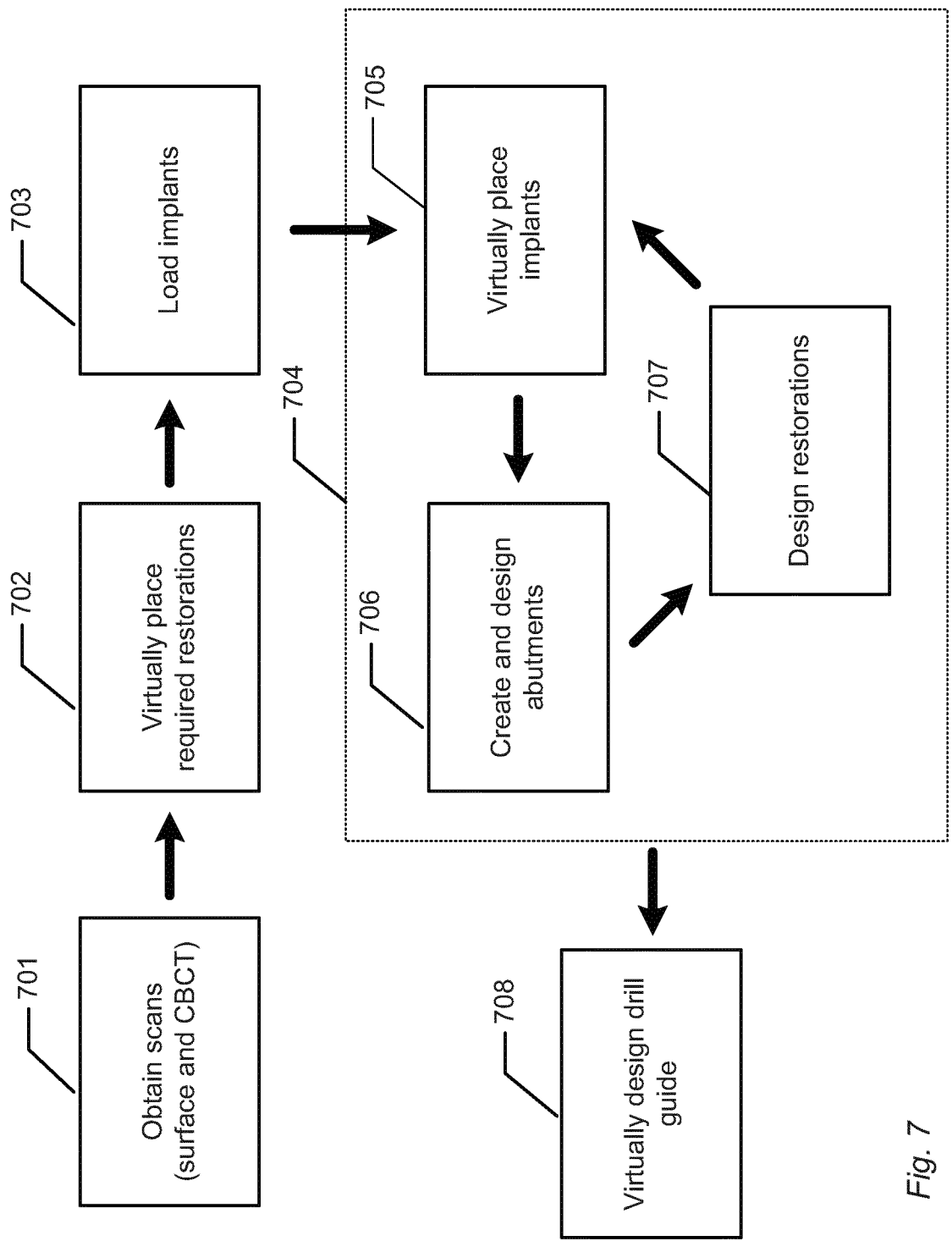
FIG. 7 shows an example of a flowchart of a method for virtually designing an implant, a restoration and more for a patient.

FIG. 7 shows an example of a flowchart of a method for virtually designing implant, restorations, and drill guide etc. for a patient.

In step 701 a CT scan, such as a CBCT scan, and a 3D surface scan of the patient's teeth are obtained and the CT scan and 3D surface scan are aligned.

In step 702 all the required restorations are virtually placed relative to the set of teeth in the aligned CT scan and 3D surface scan. The restorations can be restorations for an implant, such as a crown or a bridge, but may also be restorations for a prepped tooth etc.

In step 703 the required or planned implants are loaded into the aligned CT and 3D surface scan.

In step 704 an iterative process is performed comprising: virtually placing the loaded implants in step 705, creating and designing abutments for the implants in step 706, where the abutments may be temporary abutments, such as customized healing abutments, and/or final abutments, such as implant abutments, and in the last step of the iterative process creating or designing final restorations and/or temporary restorations, such as crowns and bridges is performed, step 707.

Finally, after the iterative process in step 704, a drill guide is virtually designed in step 708 and may be manufactured using direct digital manufacturing equipment.

Figure 8:
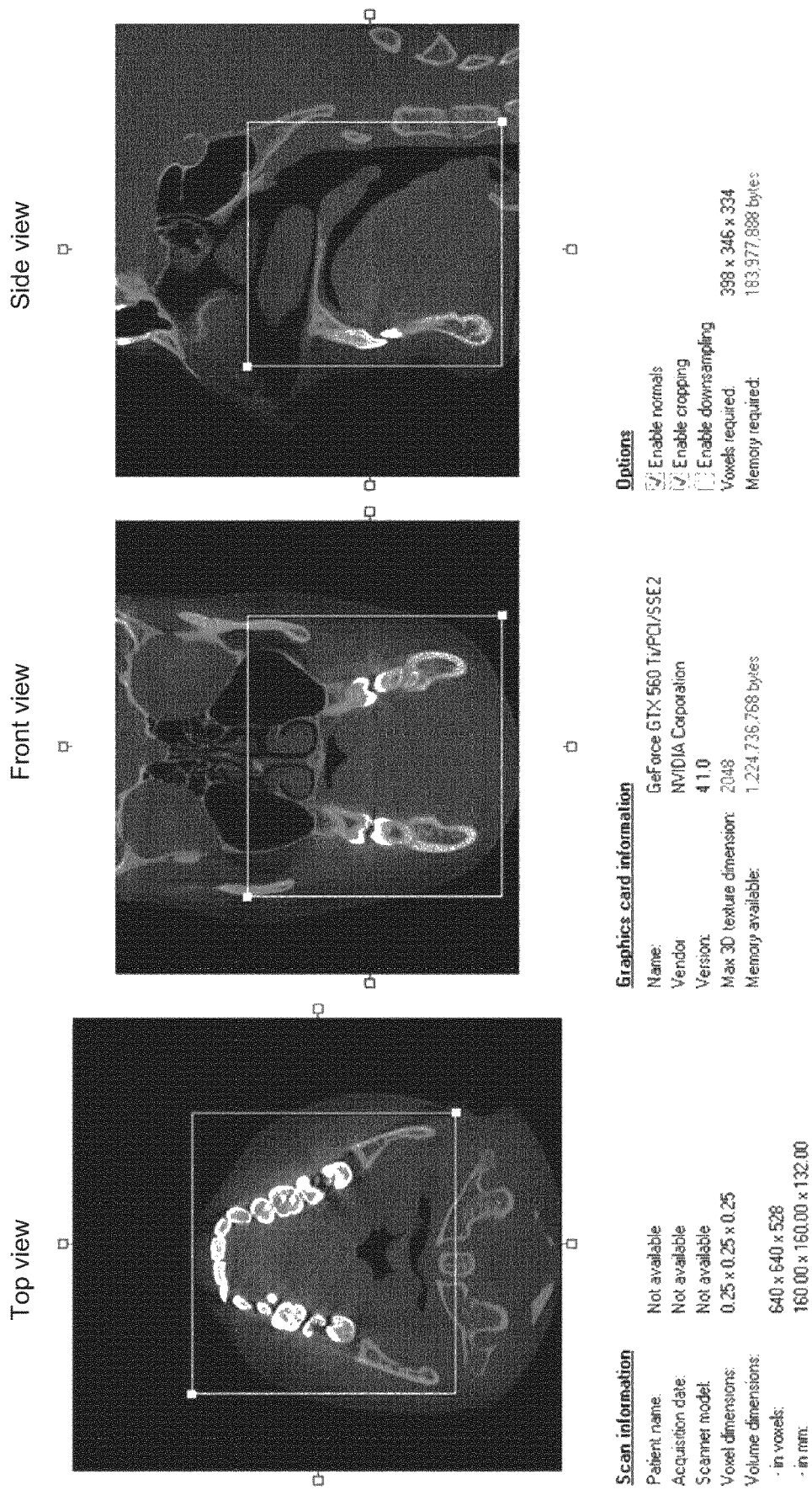
FIG. 8 shows an example of a screen view of a CT scan of a patient's set of teeth.

FIG. 8 shows an example of a screen view of a CT scan of a patient's set of teeth.

The CT scan can be viewed from different directions, such as a top view of the teeth, a front view of the teeth, and a side view of the teeth.

The screen view further shows scan information, graphics card information and options. Alternatively and/or additionally, further view directions and/or further information may be shown.

FIG. 9 shows an example of a CT scan and a 3D surface scan, which are aligned.

Figure 9A:
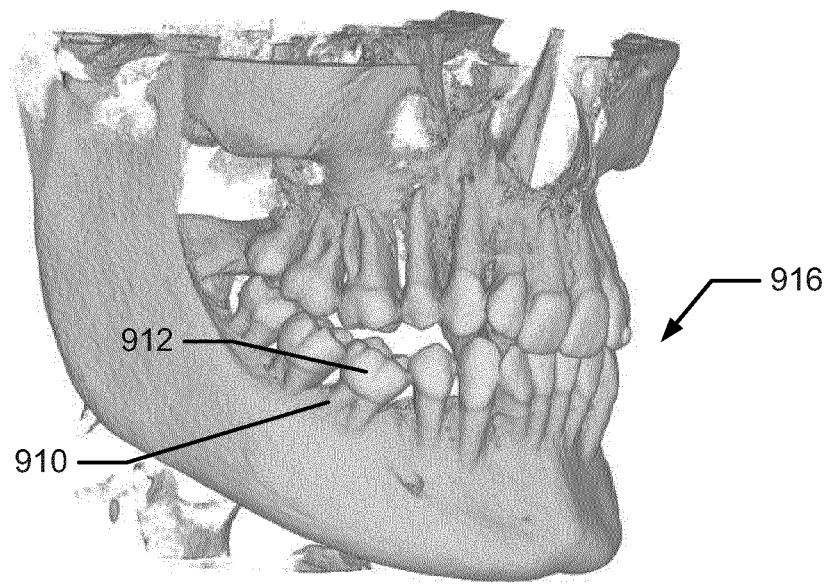
FIG. 9 shows an example of a CT scan and a 3D surface scan, which are aligned.

In FIG. 9*a*) a CT scan 916 of a patient's set of teeth is shown. Teeth 912 are seen and the teeth roots 910 of the teeth are clearly seen in the CT scan.

Figure 9B:
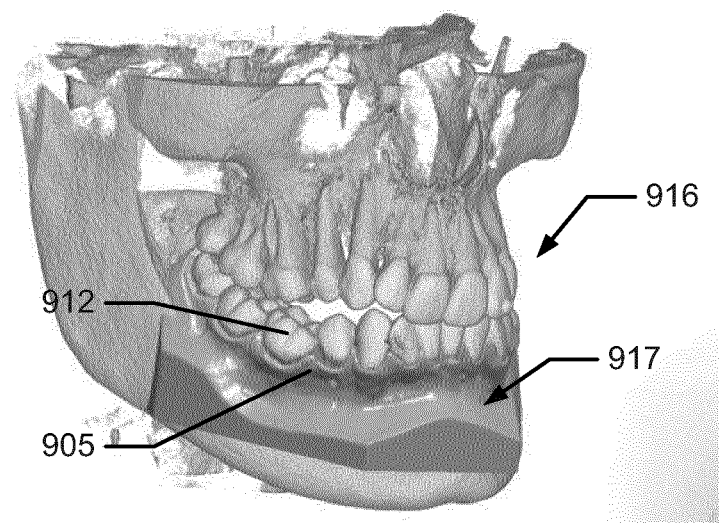

In FIG. 9*b*) a 3D surface scan 917 of the patient's set of teeth is aligned relative to the CT scan 916. The 3D surface scan provides information on the soft tissue 905, such as the gingiva around the teeth 912, which may not be derived from the CT scan.

Figure 10:
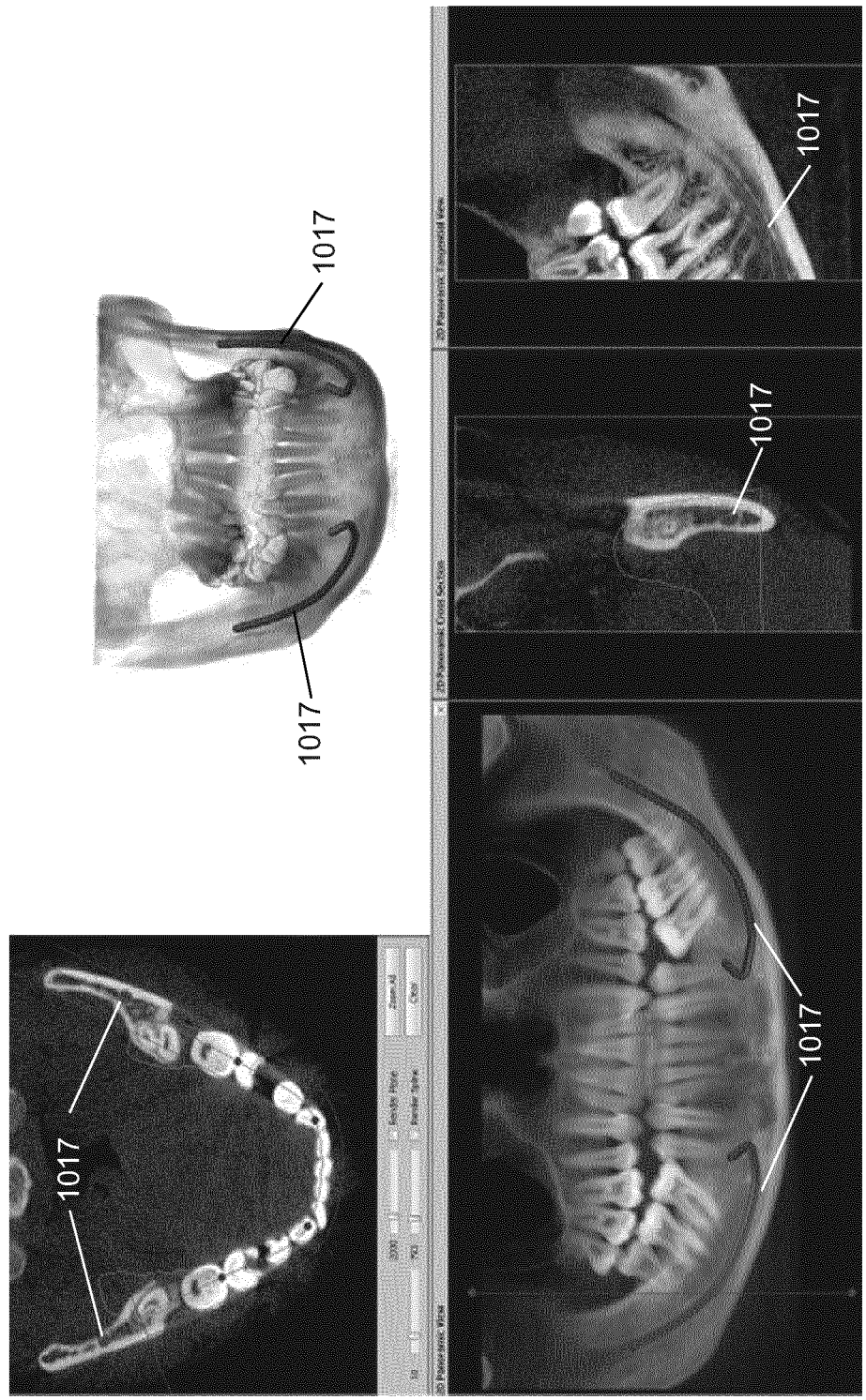
FIG. 10 shows an example of a CT scan where a nerve is seen.

FIG. 10 shows an example of a CT scan where a nerve is indicated.

FIG. 10 shows different views of the CT scan, such as a 2D panoramic axial view in the upper left corner; a 2D panoramic view in the lower left corner; a 2D panoramic cross section in the lower centre; a 2D panoramic tangential view in the lower right corner; and the full 3D model in the upper right corner. The nerve 1017 is indicated by lines or dots in the different views. When the dentist or assistants looks at these scan, the nerve will typically be in color so that it is easy to distinguish from the rest of the features in the scan.

Figure 11:
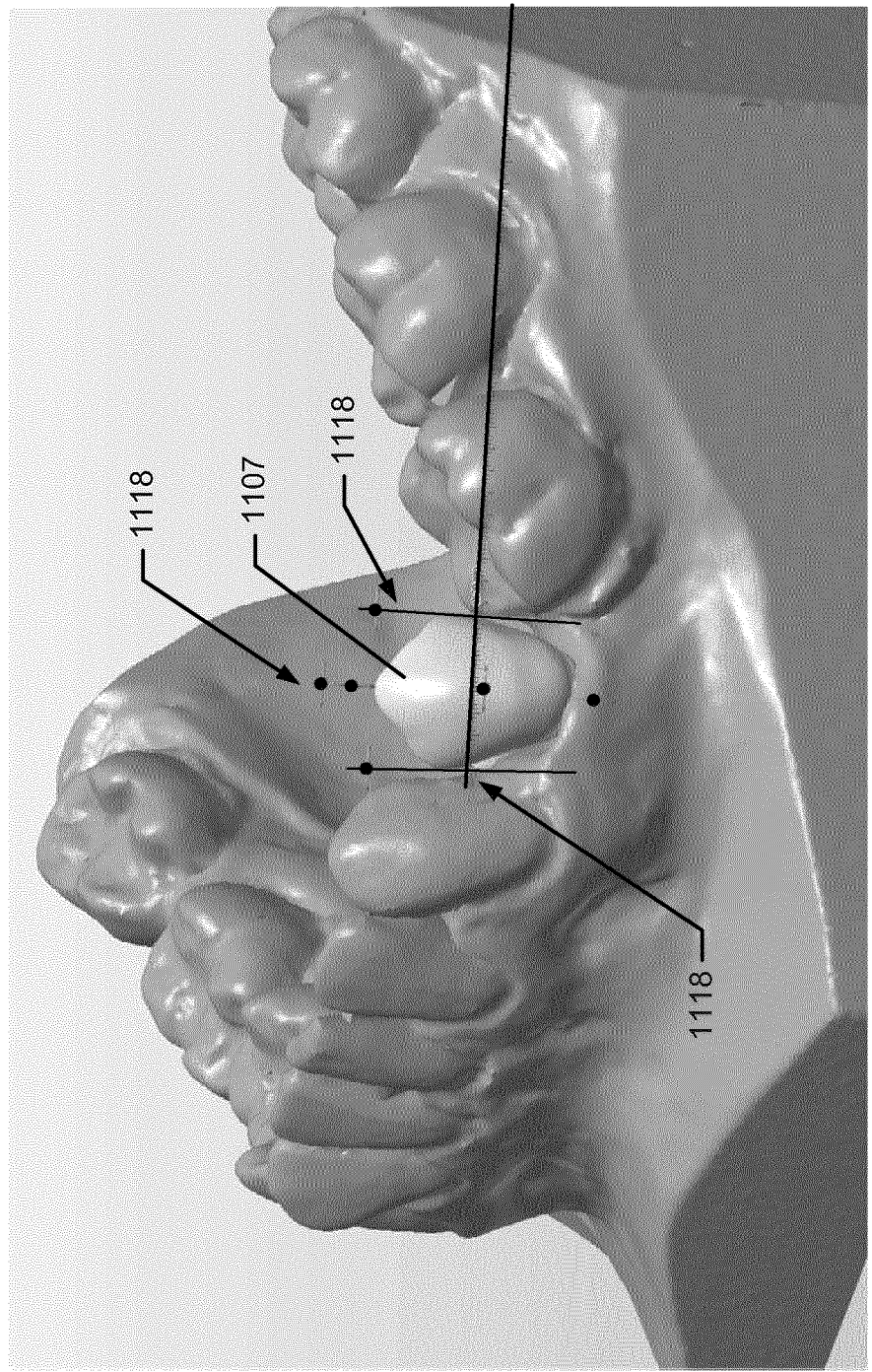
FIG. 11 shows an example of virtually placing a final restoration for an implant.

FIG. 11 shows an example of virtually placing a final restoration for an implant relative to a set of teeth.

The restoration 1107 is in the form of a crown and is virtually placed in a position in the patient's set of teeth where it replaces an original tooth. The set of teeth is here represented by a 3D surface scan obtained e.g. by intraoral scanning using e.g. the 3Shape TRIOS intraoral scanner.

Different tools 1118, such as control points and lines, for virtually designing the restoration 1107 are shown. By means of the tools 1118 the virtual restoration 1107 can be made higher, lower, wider, narrower, thicker, or it's shape can be morphed etc.

Figure 12:
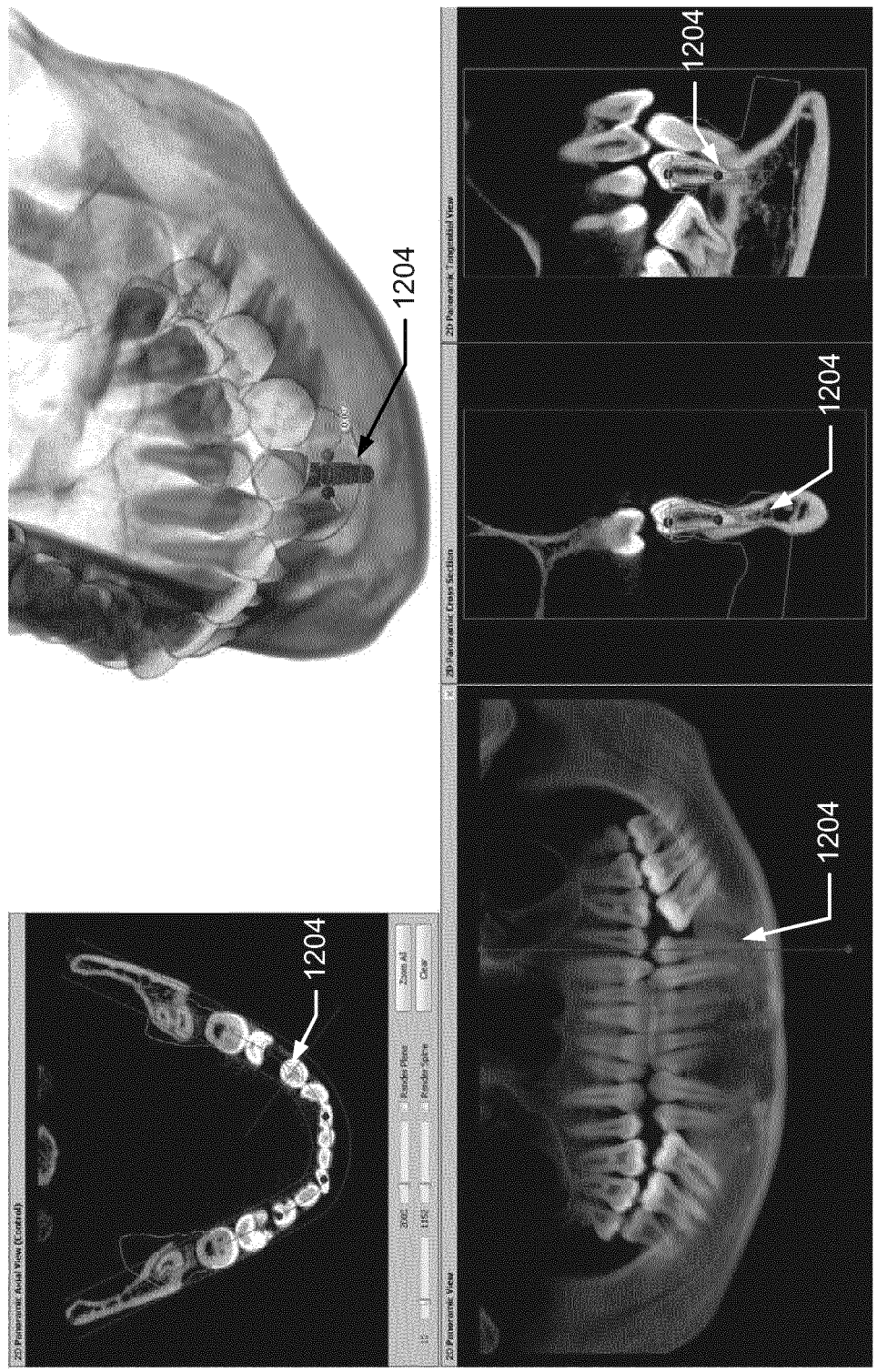
FIG. 12 shows an example of a CT scan where an implant is virtually placed.

FIG. 12 shows an example of a CT scan where an implant is virtually placed.

FIG. 12 shows different views of the CT scan, such as a 2D panoramic axial view in the upper left corner; a 2D panoramic view in the lower left corner; a 2D panoramic cross section in the lower centre; a 2D panoramic tangential view in the lower right corner; and the full 3D model in the upper right corner. The implant 1204 is indicated by full lines or contour in the different views. When the dentist or assistants looks at these scan, the implant will typically be in color so that it is easy to distinguish from the rest of the features in the scan. The views of FIG. 12 can be presented to an operator, such as a dentist or a dental technician, on a monitor of a computer system. The computer system also comprises a pointing tool, such as a computer mouse, which can be used when virtually placing the implant relative to the jaw bone of the CT scan. The computer system often comprises software code stored on a computer readable medium where the software code is configured for updating the other views seen in FIG. 12 when the placement of the implant in one view is changed by the operator using e.g. the computer mouse.

The CT scan can be a Cone Beam CT (CBCT) scan obtained using e.g. the I-CAT Cone Beam CT scanner or the Galileos scanner manufactured by Sirona FIG. 13 shows examples of virtually designing an abutment and a restoration for an implant.

Figure 13A:
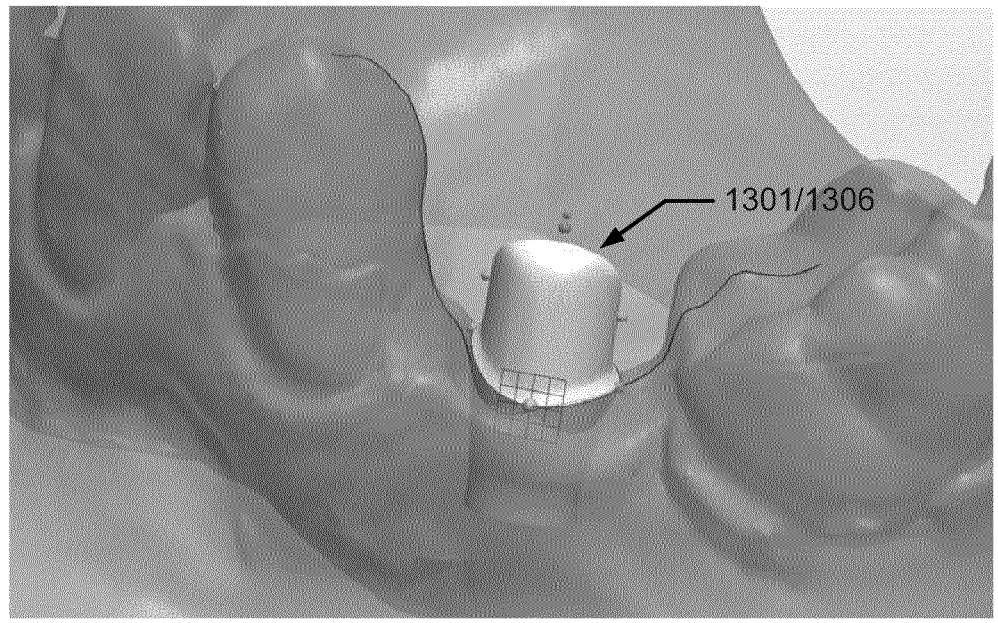
FIG. 13 shows examples of virtually designing an abutment and a restoration for an implant.

In FIG. 13*a*) an abutment is virtually designed. The abutment may be a customized healing abutment 1301 or an implant abutment 1306 for a final restoration.

Figure 13B:
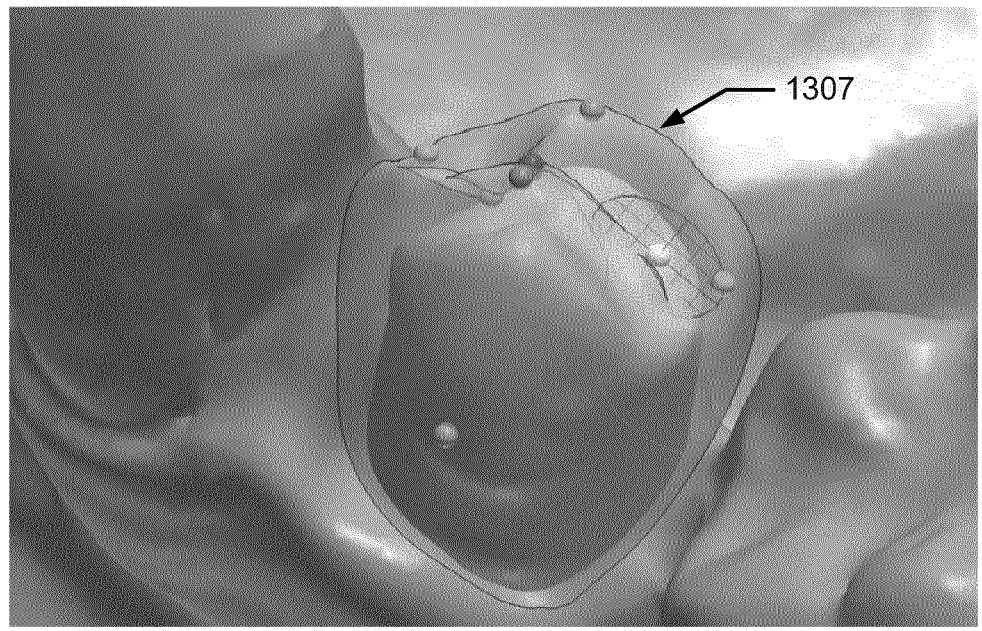

In FIG. 13*b*) a restoration is virtually designed. The restoration may be a temporary restoration for the implant during the healing period of the implant, or the restoration may be a final restoration 1307 for the implant.

FIG. 14 shows an example of a manufactured drill guide for drilling holes for implants in a patient's jaw. The drill guide has three ports for accepting means for securing the drill guide relative to the patient's jaw bone and four apertures through which the surgical drill engages the jaw bone.

FIG. 15 shows an example of a customized healing abutment 1501 with scan markers 1519 for detecting the position and orientation of the implant 1504 which the customized healing abutment is arranged in.

Figure 16:
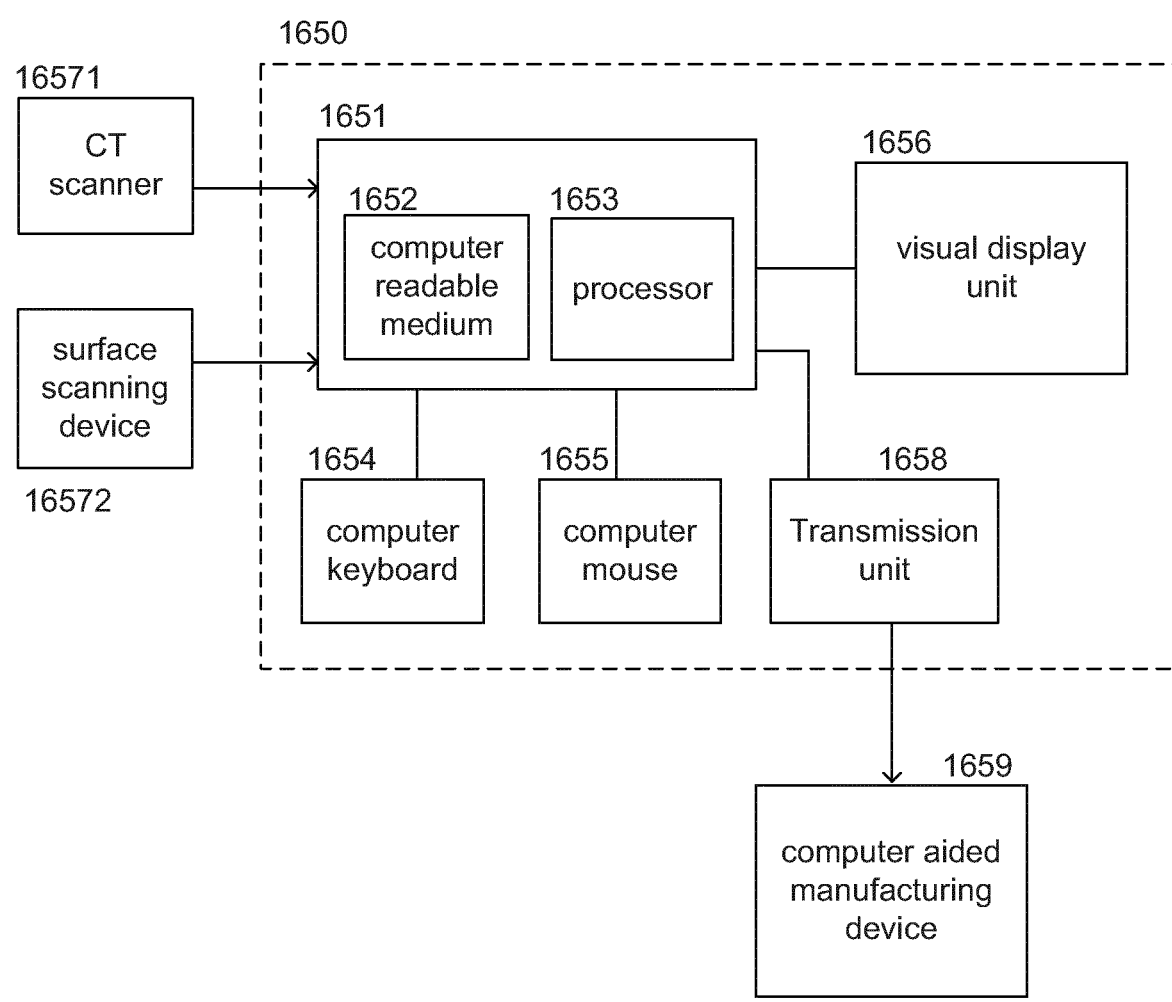
FIG. 16 shows a schematic of a system for implementing embodiments of the present invention.

FIG. 16 shows a schematic of a system for implementing embodiments of the present invention.

The system 1650 comprises a computer device 1651 comprising a computer readable medium 1652 and a processor 1653. The system further comprises a visual display unit 1656, a computer keyboard 1654 and a computer mouse 1655 for entering data, activating virtual buttons and moving virtual control points visualized on the visual display unit 1656. The visual display unit 1656 can be a computer screen. The computer device 1651 is capable of receiving a CT scan of the patient's set of teeth from a CT scanning device 16571 or capable of receiving scan data from such a scanning device and forming a CT scan of the patient's set of teeth based on such scan data. The computer device 1651 is also capable of receiving a 3D surface scan of the patient's set of teeth from a surface scanning device 16572, such as the TRIOS intra-oral scanner manufactured by 3shape NS, or capable of receiving scan data from such a scanning device and forming a 3D surface scan of the patient's set of teeth based on such scan data. The received or formed CT scan and 3D surface scan can be stored in the computer readable medium 1652 and provided to the processor 1653. The processor 1653 is configured for aligning the CT scan and the 3D surface scan, for virtually placing at least one implant relative to the CT scan of the teeth; and for virtually designing a customized healing abutment based on the CT scan using the method according to any of the embodiments. In the designing of the customized healing abutment and in virtual placing the implant, one or more options can be presented to the operator. The options can be presented in a user interface visualized on the visual display unit 1656.

The processor 1653 may also be configured for designing a drill guide for the surgical drilling of a bore in the patient's jaw bone to make space for the implant. The system then comprises a unit 1658 for transmitting a designed virtual 3D model of the drill guide to e.g. a computer aided manufacturing (CAM) device 1659 for manufacturing the drill guide or to another computer system e.g. located at a remote fabrication center, where the drill guide is manufactured. The unit for transmitting the virtual 3D model can be a wired or a wireless connection.

FIG. 17 shows flowcharts of embodiments of the inventive method.

Figure 17A:
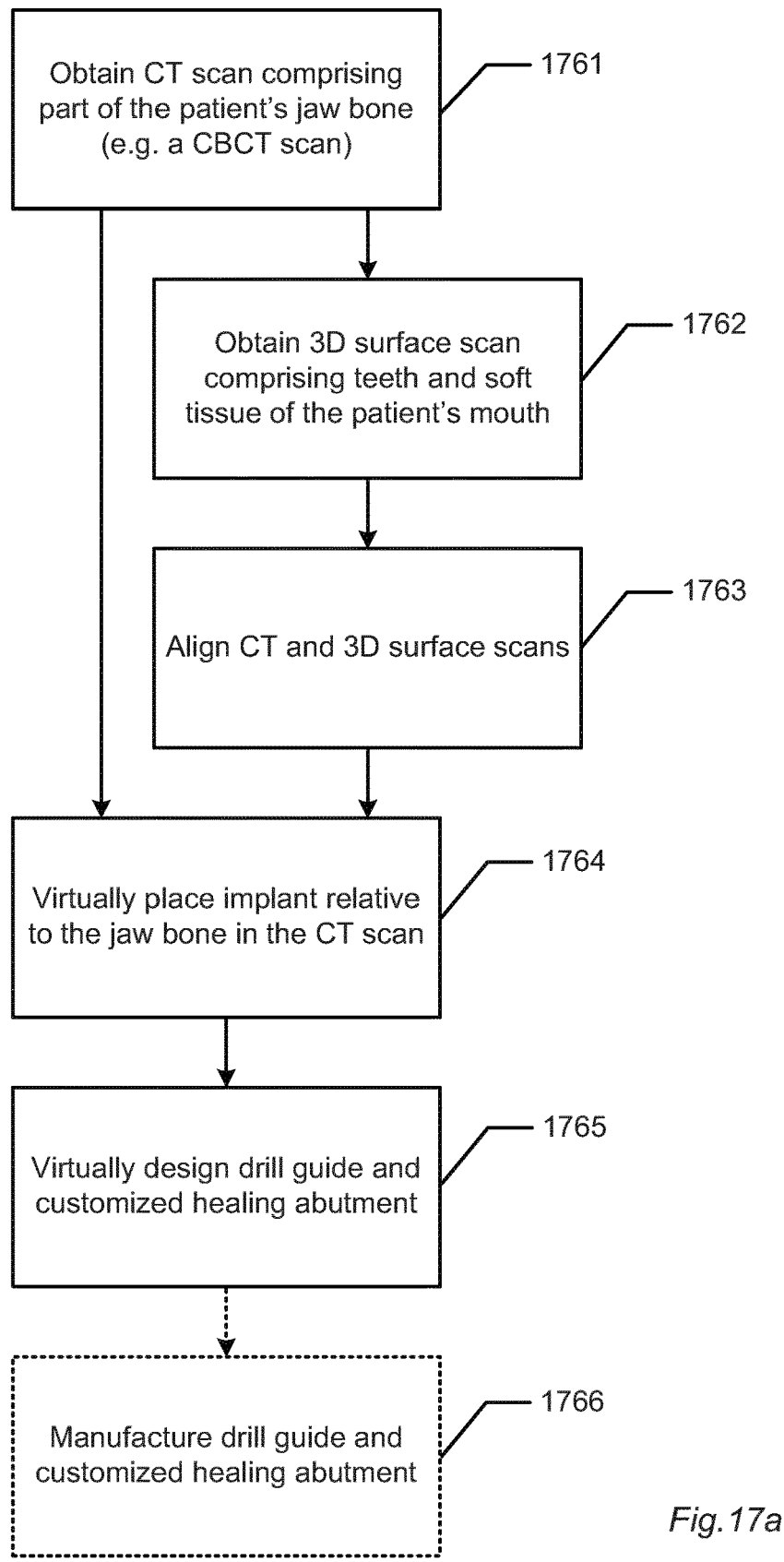
FIG. 17 shows flowcharts of embodiments of the inventive method.

FIG. 17a shows an embodiment 1760 where the drill guide and the customized healing abutment, are virtually designed based on aligned CT and 3D surface scans. The components are subsequently manufactured based on the designs using direct digital manufacture techniques.

In step 1761 a CT scan comprising at least part of the patient's jaw bone is obtained. When the patient has teeth in his mouth, the CT scan may also comprise the teeth and their roots. The CT scan can be a Cone Beam CT (CBCT) scan obtained using e.g. the I-CAT Cone Beam CT scanner or the Galileos scanner manufactured by Sirona.

Optionally a 3D surface scan comprising teeth and soft tissue of the patient's mouth is also obtained in step 1762 using e.g. the TRIOS intraoral scanner manufactured by 3shape A/S. The obtained CT and 3D surface scans are then aligned in step 1763 using e.g. a computer implemented iterative closest point algorithm. The combination of the two scans provide a virtual representation of the patient's mouth with even more information than the CT scan alone, such that e.g. the soft tissue can be represented with higher resolution and precision in the combined representation. This was also illustrated in FIG. 9.

In step 1764 the implant is virtually placed relative to the jaw bone in the CT scan such that it is arranged according to a planned implant placement. This may be done manually by the operator using a pointing tool, such as a computer mouse, of a computer system adapted for carrying out the method, or it may be done automatically using computer implemented algorithms configured for determining an appropriate orientation and location relative to the jaw bone. The implant placement may be optimized with respect to the adequateness of the jaw bone for supporting the implant and with respect to insertion directions for the implant into the bore which is to be drilled into the jaw bone.

In 1765 the drill guide and customized healing abutment are designed, where the design of the drill guide and of the customized healing abutment is at least partly based on the CT scan and on the planned implant placement. The a drill guide is designed for guiding the surgical drilling of a bore for the implant into the patient's jaw bone at the planned implant placement, while the customized healing abutment is configured for shaping the soft tissue according to a target profile when arranged in the implant.

When designed, the drill guide and of the customized healing abutment can be manufactured using direct digital manufacture techniques such as 3D printing or milling in step 1766. This step may be performed at a separate system or facility, such as a specialized dental laboratory.

Figure 17B:
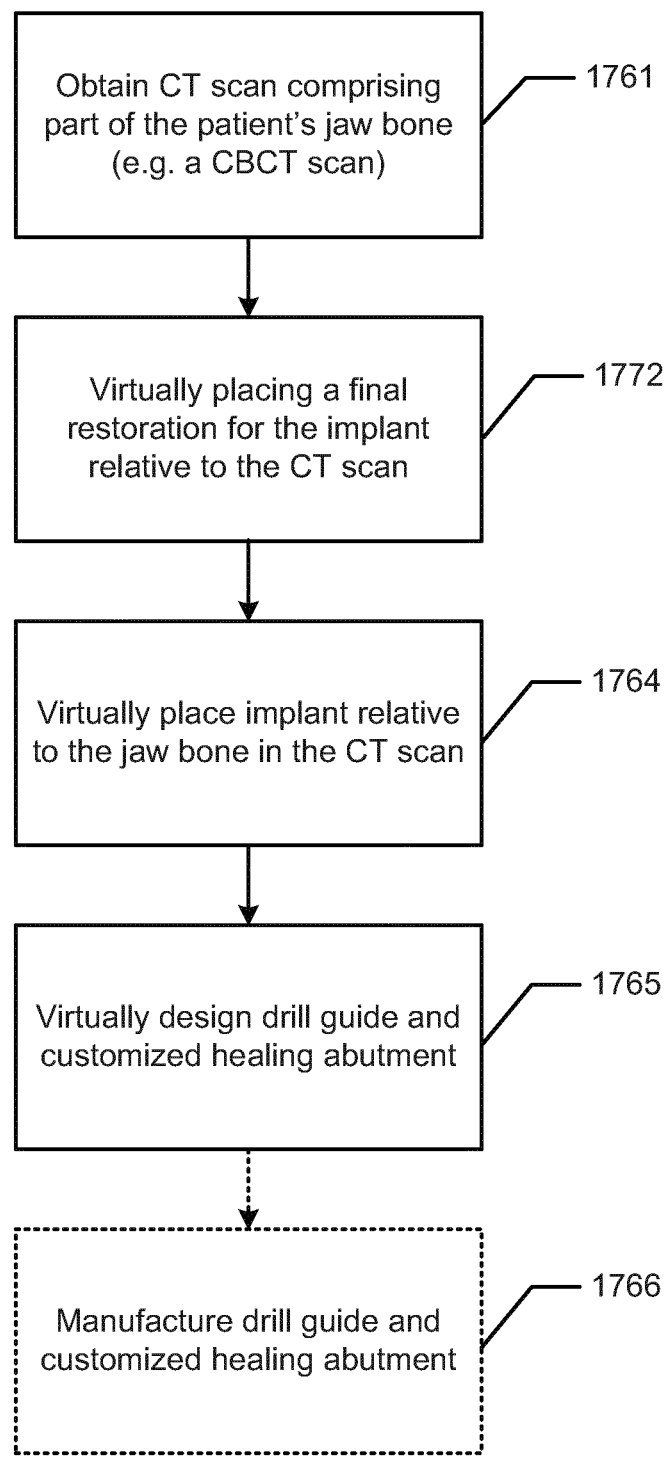

FIG. 17b shows an embodiment 1767 where the designing comprises virtually placing a final restoration for the implant before virtually placing the implant relative to the CT scan.

In step 1761 a CT scan comprising at least part of the patient's jaw bone is obtained. When the patient has teeth in his mouth, the CT scan may also comprise the teeth and their roots. The CT scan can be a Cone Beam CT (CBCT) scan obtained using e.g. the I-CAT Cone Beam CT scanner or the Galileos scanner manufactured by Sirona.

In step 1772 a final restoration for the implant is designed and virtually placed relative to the CT scan. The final restoration can be designed to achieve the best possible aesthetic appearance when the manufactured restoration later is connected to the implant in the patient's mouth.

In step 1764 the implant is virtually placed relative to the jaw bone in the CT scan such that it is arranged according to a planned implant placement. This may be done manually by the operator using a pointing tool, such as a computer mouse, of a computer system adapted for carrying out the method, or it may be done automatically using computer implemented algorithms configured for determining an appropriate orientation and location relative to the jaw bone. The implant placement may be optimized with respect to the adequateness of the jaw bone for supporting the implant and with respect to insertion directions for the implant into the bore which is to be drilled into the jaw bone. With the final restoration already being placed in relation to the CT scan, it can also be taken into account when virtually inserting the implant and determining the planned implant placement. One advantage of this is that the planned implant placement can be adapted to provide that the implant can support the final restoration in the mouth when the final restoration is shaped as designed in step 1772. The implant placement is thus optimized with respect to obtaining an aesthetic final restoration and with respect to obtaining a good mechanical function of the implant in the jaw bone.

In 1765 the drill guide and customized healing abutment are designed, where the design of the drill guide and of the customized healing abutment is at least partly based on the CT scan and on the planned implant placement. The a drill guide is designed for guiding the surgical drilling of a bore for the implant into the patient's jaw bone at the planned implant placement, while the customized healing abutment is configured for shaping the soft tissue according to a target profile when arranged in the implant. When designed, the drill guide and of the customized healing abutment can be manufactured using direct digital manufacture techniques such as 3D printing or milling in step 1766. This step may be performed at a separate system or facility, such as a specialized dental laboratory.

In some embodiments, the steps of 17a and 17b are combined such that the customized healing abutment and the drill guide are virtually designed based on a combination of a 3D surface scan and a CT scan comprising the patient's jaw bone, where the final restoration has been virtually arranged relative to the CT scan before the implant.

Figure 19:
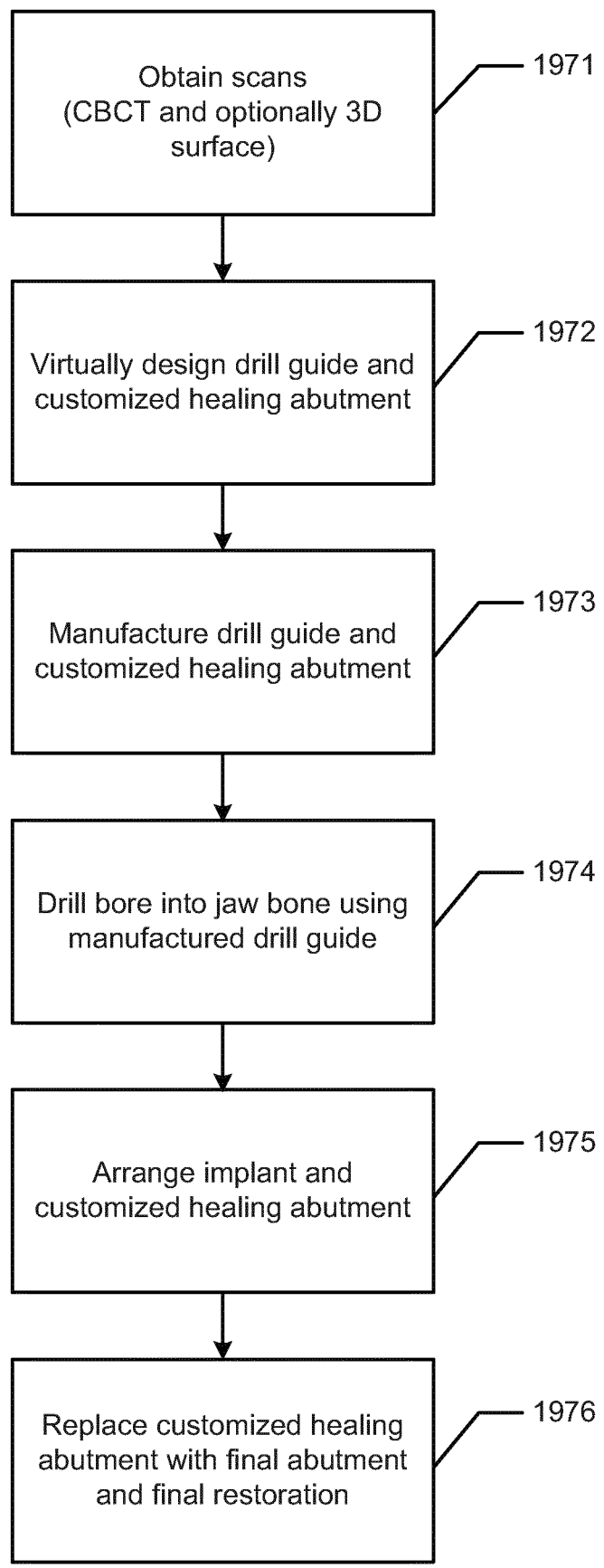
FIG. 19 shows a flowchart for a treatment of a patient providing the patient with an implant based final restoration.

FIG. 19 shows a flowchart for procedure for extracting a tooth and replacing it with an implant and a corresponding final restoration.

In 1971 a CT scan comprising at least part of the patient's jaw bone is obtained. When the patient has teeth in his mouth, the CT scan may also comprise the teeth and their roots. Optionally a 3D surface scan comprising at least part of the teeth and at least part of the soft tissue of the patient's mouth is also obtained.

In 1972, a drill guide is virtually designed for guiding the surgical drilling of a bore for the implant into the patient's jaw bone and a customized healing abutment is virtually designed for shaping the soft tissue at the drilled bore. This can be done before the tooth is extracted. The designing comprises virtually placing the implant relative to the teeth of the CT scan and ensures that the physical implant arranged in a bore drilled using the drill guide is placed according to the virtual implant placement and that the customized healing abutment can shape the soft tissue according to a target profile when arranged in the implant.

The target profile of the soft tissue can be determined from the desired emergence profile of the final restoration for the implant. Based on the designs, the drill guide and the customized healing abutment can be manufactured using direct digital manufacturing such as 3D printing or milling.

In step 1973, the drill guide and the customized healing abutment are manufactured based on the designs using e.g. 3D printer or a milling machine.

In step 1974, the bore is drilled into the patients jaw bone using the manufactured drill guide.

In step 1975, the implant is arranged in the bore and the customized healing abutment is arranged in the implant. If a temporary restoration has been designed and manufactured, it is secured at the customized healing abutment.

The customized healing abutment stays in the implant while the implant heals to the jaw bone through osseointegration. During the healing the soft tissue takes the form dictated by the surface of the customized healing abutment such that the soft tissue can be shaped according to a target profile. The target profile is chosen such that the shaped soft tissue follows a desired emergence of a final restoration/final abutment for the implant. If the final restoration and final abutment has been designed and manufactured earlier in the process, these can then be arranged in the patient's mouth once the healing is complete, with the final abutment secured in the implant and the final restoration cemented to the final abutment. In 1976 the customized healing abutment is removed from the implant and a final abutment is arranged in the implant. The final restoration is then cemented to the final abutment.

With the present invention where the drill guide and the customized healing abutment are designed to ensure that an implant arranged in a bore drilled into the patients jaw bone using the drill guide is placed according to the virtual implant placement and the customized healing abutment is designed to shape the soft tissue according to the target profile when arranged in the implant, the steps 1972 to 1975 can potentially be performed during a single visit to the dentist. After having discussed the situation with the patient based on the scans, the drill guide and the customized healing abutment are designed and manufactured while the dentist prepares the patient for the drilling, i.e. administrating anesthetics and extracting the original tooth. The drill guide is then used for the surgical drilling and the customized healing abutment is arranged in the implant that is placed in the drilled bore.

In fact step 1971 can also be performed during this single visit. But often the dentist prefers to have obtained and evaluated the scans prior to the visit where the surgical drilling takes place.

The final restoration can be designed and manufactured together with the design and manufacture of the drill guide and the customized healing abutment, such that the drill guide and the customized healing abutment are designed based on the final restoration and such that the designing is completed in one run. This approach assumes that the implant placement in the jaw bone during osseointegration does not change. In some cases where the dentist decides that there is a large risk of the implant move during healing of the implant to the jaw bone, he may choose to wait until the healing is final and then obtain a second CT scan of the customized healing abutment and the surrounding teeth. Form the second CT scan he can then design the final abutment and final restoration taken into account the exact position and orientation of the implant relative to the patient's teeth.

FIG. 20 shows a design of the customized healing abutment where the transition to the implant screw is smooth. The figures here are illustrations of cross sectional views of the oral situation and the implant as seen from a neighboring tooth.

FIG. 20a shows the implant 2004 arranged in the patient's jaw bone 2011 and the surrounding gingiva 2005. The customized healing abutment 2001 is arranged at the implant 2004 such that bores 2092 of the two are aligned. The customized healing abutment 2001 has an uppermost surface 2090 comprising an opening 2091 for the head of the implant screw FIG. 20b shows an implant screw 2093 with a screw head 2094 and a screw body 2095. The screw head has a height Hhead and the screw body a height Hbody along the longitudinal axis of the screw 2093.

FIG. 20c shows the situation where the customized healing abutment 2001 is secured to the implant 2004 using the implant screw having a body 2095 which extends along the bores of the customized healing abutment and implant. The customized healing abutment is virtually designed taking into account information relating to the implant screw, such that the customized healing abutment is designed to provide a smooth transition 2096 between the uppermost surface 2090 of the customized healing abutment and the uppermost surface of the screw head 2094. As seen in the figure, the customized healing abutment 2001 is designed such that the screw head 2094 completely covers the opening in the uppermost surface of the customized healing abutment 2001 and the screw head 2094 completely covers the sidewall of the opening when the manufactured customized healing abutment is connected to the implant in the patient's jaw 2011 using the implant screw 2093. Likewise, the sidewall of the screw head 2094 cannot be seen when the transition 2096 is smooth. The smooth transition may be such that the uppermost surfaces of the customized healing abutment and of the implant screw head are in the same plane when the implant screw is arranged in relation to the customized healing abutment. The designing of the customized healing abutment can be such that setting the height of the opening at a value identical to the screw head height Hhead such that the screw head does not extend above the uppermost surface of the customized healing abutment or vice versa.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

Embodiments

1. A method of virtually designing a customized healing abutment and a drill guide for a patient, where the method comprises:
   obtaining a CT scan comprising at least part of the patient's jaw bone;
   virtually placing at least one implant relative to the jaw bone in the CT scan such that a planned implant placement is defined; and
   virtually designing:
      a drill guide for guiding the surgical drilling of a bore for the implant into the patient's jaw bone at the planned implant placement; and
      a customized healing abutment configured for shaping the soft tissue according to a target profile when arranged in the implant;
where the design of the drill guide and of the customized healing abutment is at least partly based on the CT scan and on the planned implant placement.

2. The method according to embodiment 1, wherein the method comprises obtaining a 3D surface scan comprising at least part of the teeth and at least part of the soft tissue of the patient's mouth.

3. The method according to any one or more of the preceding embodiments, wherein the method comprises performing an alignment of the CT scan and the 3D surface scan before designing the customized healing abutment and the drill guide.

4. The method according to any one or more of the preceding embodiments, wherein the alignment comprises selecting three corresponding points on the CT scan and on the 3D surface scan.

5. The method according to any one or more of the preceding embodiments, wherein the alignment comprises using the computer-implemented method of iterative closets point.

6. The method according to any one or more of the preceding embodiments, wherein the drill guide and the customized healing abutment are designed simultaneously.

7. The method according to any one or more of the preceding embodiments, wherein the CT scan is a preoperative CT scan obtained prior to the surgical drilling into the patient's jaw bone and/or wherein the 3D surface scan is a preoperative 3D surface scan obtained prior to the surgical drilling into the patient's jaw bone.

8. The method according to any one or more of the preceding embodiments, wherein the method comprises virtually placing a final restoration for the implant.

9. The method according to any one or more of the preceding embodiments, wherein the final restoration is virtually placed before virtually placing the implant.

10. The method according to any one or more of the preceding embodiments, wherein the method comprises virtually designing the final restoration, such as a crown, bridge, or denture.

11. The method according to any one or more of the preceding embodiments, wherein the method comprises using the shape of the original tooth to design the final restoration.

12. The method according to any one or more of the preceding embodiments, wherein the design of final restoration is at least partly based on the design of the customized healing abutment.

13. The method according to any one or more of the preceding embodiments, wherein the final restoration comprises a sub-gingival portion, and the sub-gingival portion is based on the design of the customized healing abutment.

14. The method according to any one or more of the preceding embodiments, wherein the method comprises virtually designing a final implant abutment for insertion into the implant, where the final restoration is adapted to be attached to the final implant abutment.

15. The method according to any one or more of the preceding embodiments, wherein the method comprises obtaining a second CT scan and/or a second 3D surface scan comprising the customized healing abutment, when placed in the mouth of the patient, and based on the second CT scan and/or the second 3D surface scan, adjusting the design of the final restoration.

16. The method according to any one or more of the preceding embodiments, wherein the customized healing abutment is adapted to be arranged at least partly in the soft tissue having a desired position and orientation relative to the implant.

17. The method according to any one or more of the preceding embodiments, wherein the design of the customized healing abutment is at least partly based on the design of the final restoration.

18. The method according to any one or more of the preceding embodiments, wherein the design of the customized healing abutment is at least partly based on a visible part of the neighbor teeth and/or on a non-visible part of the neighbor teeth.

19. The method according to any one or more of the preceding embodiments, wherein the design of the customized healing abutment is at least partly based on the soft tissue at the place where the customized healing abutment is adapted to be arranged.

20. The method according to any one or more of the preceding embodiments, wherein the design of the customized healing abutment is at least partly based on a desired shape of the soft tissue between the implant and the final restoration.

21. The method according to any one or more of the preceding embodiments, wherein the method comprises virtually designing the emergence profile of the customized healing abutment from the top of the implant to the beginning of the gingiva.

22. The method according to any one or more of the preceding embodiments, wherein the method comprises using the shape of the original tooth to design the customized healing abutment.

23. The method according to any one or more of the preceding embodiments, wherein the designed customized healing abutment comprises a substantially flat, rounded off top.

24. The method according to any one or more of the preceding embodiments, wherein the customized healing abutment is designed to be level with the surrounding soft tissue.

25. The method according to any one or more of the preceding embodiments, wherein the customized healing abutment is designed to have a predetermined height relative to the surrounding soft tissue.

26. The method according to any one or more of the preceding embodiments, wherein the design of the customized healing abutment is not adapted for attachment of a temporary crown or other temporary restoration.

27. The method according to any one or more of the preceding embodiments, wherein the design of the customized healing abutment comprises scan markers for deriving information of the implant position and orientation when scanning the customized healing abutment in the implant.

28. The method according to any one or more of the preceding embodiments, wherein the scan markers and their position on the customized healing abutment are virtually designed for matching the customized healing abutment.

29. The method according to any one or more of the preceding embodiments, wherein the method comprises virtually designing the insertion of the implant in the patient's mouth.

30. The method according to any one or more of the preceding embodiments, wherein the method comprises using the shape of the original tooth to design the planned implant placement position and orientation.

31. The method according to any one or more of the preceding embodiments, wherein the design of the virtual implant provides that the implant is adapted to be inserted in the jaw bone of the patient with the planned implant placement being such that the implant is not placed in a tooth root from another tooth or in a nerve.

32. The method according to any one or more of the preceding embodiments, wherein the method comprises virtually performing collision detection of the implant with respect to neighbor teeth roots or implants.

33. The method according to any one or more of the preceding embodiments, wherein the method comprises virtually providing limitations for the implant relative to the visible part of the neighbor teeth.

34. The method according to any one or more of the preceding embodiments, wherein the method comprises virtually planning the surgical drilling of the bore for the implant.

35. The method according to any one or more of the preceding embodiments, wherein the virtual planning of the surgical drilling is designed based on the CT scan.

36. The method according to any one or more of the preceding embodiments, wherein the virtual planning of the surgical drilling and/or virtual design of the drill guide is/are designed based on the 3D surface scan.

37. The method according to any one or more of the preceding embodiments, wherein the method comprises virtually extracting any teeth which are placed where an implant is planned to be arranged.

38. The method according to any one or more of the preceding embodiments, wherein the method comprises virtually designing the soft tissue surrounding the customized healing abutment.

39. The method according to any one or more of the preceding embodiments, wherein the method comprises virtually designing the soft tissue surrounding the customized healing abutment by using the shape of the original soft tissue from the CT scan and/or the 3D surface scan.

40. The method according to any one or more of the preceding embodiments, wherein the design of the customized healing abutment is configured for attachment of a temporary restoration to the customized healing abutment.

41. The method according to any one or more of the preceding embodiments, wherein the design of the customized healing abutment comprises means for attachment of a temporary restoration, such as a temporary crown or a temporary bridge.

42. The method according to any one or more of the preceding embodiments, wherein the customized healing abutment comprises a screw hole for retaining the temporary restoration, such as temporary crown.

43. The method according to any one or more of the preceding embodiments, wherein the temporary restoration, such as a temporary crown, is adapted to be cemented to the customized healing abutment.

44. The method according to any one or more of the preceding embodiments, wherein the method comprises virtually designing a temporary restoration for attachment to the customized healing abutment.

45. The method according to any one or more of the preceding embodiments, wherein the CT scan is a cone-beam CT scan (CBCT scan).

46. The method according to any one or more of the preceding embodiments, wherein the 3D surface scan is an intra-oral scan captured directly in the patient's mouth, and/or a scan of a physical impression of the patient's teeth/gums, and/or a scan of a physical model of the patient's teeth/gums.

47. The method according to any one or more of the preceding embodiments, wherein the method comprises virtually designing a radiographic template adapted for placement on the patient's teeth to simulate the implant position and/or the final restoration.

48. The method according to any one or more of the preceding embodiments, wherein the method comprises obtaining a CT scan and/or a 3D surface scan of a radiographic template arranged on the patient's teeth.

49. The method according to any one or more of the preceding embodiments, wherein virtually placing the implant and virtually designing the customized healing abutment are performed as part of an iterative process where each iteration of the iterative process comprises evaluating the implant placement and/or the customized healing abutment design and based on a result of the evaluation determining whether the implant placement and/or the customized healing abutment design must be modified.

50. The method according to any one or more of the preceding embodiments, where the evaluation of the iterative process takes into account the design of the final restoration.

51. The method according to any one or more of the preceding embodiments, where virtually designing the final restoration is part of the iterative process and where the evaluation determines whether the design of the final restoration must be modified.

52. The method according to any one or more of the preceding embodiments where the implant placement is modified based on the designed customized healing abutment and/or based on the designed final restoration.

53. The method according to any one or more of the preceding embodiments wherein the customized healing abutment is redesigned based on the modified implant placement and/or based on the designed final restoration.

54. The method according to any one or more of the preceding embodiments, where the iterative process comprises redesigning the final restoration based on the modified implant placement and/or on the redesigned customized healing abutment.

55. The method according to any one or more of the preceding embodiments, where the drill guide is virtually designed based on the planned implant placement after the last iteration of the iterative process.

56. A user interface for virtually designing a customized healing abutment and a drill guide for a patient, where the user interface is configured for:
- obtaining and visualizing a CT scan comprising at least part of the patient's jaw bone;
- virtually placing at least one implant relative to the jaw bone of the CT scan such that a planned implant placement is defined; and
- virtually designing:
  - a drill guide for guiding the surgical drilling of a bore for the implant into the patient's jaw bone at the planned implant placement; and
  - a customized healing abutment configured for shaping the soft tissue according to a target profile when arranged in the implant where the design of the drill guide and the customized healing abutment is at least partly based on the CT scan and on the planned implant placement.

57. The user interface according to embodiment 56, wherein the user interface is configured for obtaining and visualizing a 3D surface scan comprising at least part of the teeth and soft tissue of the patient's mouth.

58. The user interface according to embodiment 56 or 57, wherein the user interface is configured for performing an alignment of the CT scan and the 3D surface scan before designing the customized healing abutment and the drill guide.

59. The user interface according to any of embodiments 56 to 58, wherein the user interface is configured for virtually placing a final restoration for the implant relative to the CT scan and/or relative to the 3D surface scan, and for virtually designing the final restoration.

60. The user interface according to any of embodiments 56 to 59, wherein the user interface is configured for virtually placing the final restoration before virtually placing the implant.

61. The user interface according to any of embodiments 56 to 60, wherein the user interface is configured for being visualized to an operator using a computer screen and for allowing the operator to enter data into and to make choices presented in the user interface by means of a computer keyboard or a computer mouse.

62. The user interface according to any of embodiments 56 to 61, wherein the user interface is configured for visualizing the implant together with the CT scan and optionally the 3D surface scan, and the user interface comprises a virtual tool for performing designing of the customized healing abutment and the drill guide when activated.

63. A method of virtually designing a customized healing abutment for a patient, where the method comprises:
- obtaining a CT scan comprising at least part of the patient's jaw bone;
- obtaining information relating to an implant screw by which the customized healing abutment is to be attached to an implant, where the implant screw comprises a screw head; and
- virtually designing a customized healing abutment taking into account the implant screw information, where an uppermost surface of the customized healing abutment is designed to comprise an opening for accommodating the screw head, and where the customized healing abutment is designed to provide a smooth transition from the customized healing abutment to the implant screw.

64. The method according to any one or more of the preceding embodiments, wherein the information relates to the height of the implant screw head, and wherein the opening of the customized healing abutment is shaped to provide that the transition from the customized healing abutment to the implant screw is smooth.

65. The method according to any one or more of the preceding embodiments, wherein the information relates to the length of the implant screw and wherein the customized healing abutment is designed to have a length which provides that the transition from the customized healing abutment to the implant screw is smooth.

66. The method according to any one or more of the preceding embodiments, wherein the customized healing abutment is designed to have a height is within an interval defined by the screw length.

67. The method according to any one or more of the preceding embodiments, wherein the customized healing abutment is virtually designed such that it is configured for shaping the soft tissue according to a target profile when arranged in the implant.

68. The method according to any one or more of the preceding embodiments, wherein the method comprises virtually placing at least one implant relative to the jaw bone in the CT scan such that a planned implant placement is defined.

The invention claimed is:

1. A method of virtually designing a customized healing abutment and a drill guide for a patient, where the method comprises:
- obtaining a 3D internal scan comprising at least part of the patient's jaw bone;
- virtually placing at least one implant relative to the jaw bone in the 3D internal scan such that a planned implant placement is defined; and
- virtually designing:
  - a drill guide for guiding the surgical drilling of a bore for the implant into the patient's jaw bone at the planned implant placement; and
  - a customized healing abutment configured for shaping the soft tissue according to a target profile when arranged in the implant;
- where the design of the drill guide and of the customized healing abutment is at least partly based on the 3D internal scan and on the planned implant placement; and
- obtaining a second scan after healing is finished; and
- virtually designing a second abutment and a final restoration based on the second scan.

2. The method according to claim 1, wherein the method comprises obtaining a 3D surface scan comprising at least part of the teeth and at least part of the soft tissue of the patient's mouth.

3. The method according to claim 2, wherein the method comprises performing an alignment of the 3D internal scan and the 3D surface scan before designing the customized healing abutment and the drill guide.

4. The method according to claim 2, wherein the 3D internal scan is a preoperative CT scan obtained prior to the surgical drilling into the patient's jaw bone and/or wherein the 3D surface scan is a preoperative 3D surface scan obtained prior to the surgical drilling into the patient's jaw bone.

5. The method according to claim 1, wherein the method comprises virtually placing the final restoration for the implant.

6. The method according to claim 5, wherein the final restoration is virtually placed before virtually placing the implant.

7. The method according to claim 1, wherein the design of the final restoration is at least partly based on the design of the customized healing abutment.

8. The method according to claim 5, wherein the final restoration comprises a sub-gingival portion, and the sub-gingival portion is based on the design of the customized healing abutment.

9. The method according to claim 1, wherein the customized healing abutment is adapted to be arranged at least partly in the soft tissue having a desired position and orientation relative to the implant.

10. The method according to claim 1, wherein the design of the customized healing abutment is at least partly based on the soft tissue at the place where the customized healing abutment is adapted to be arranged.

11. The method according to claim 5, wherein the design of the customized healing abutment is at least partly based on a desired shape of the soft tissue between the implant and the final restoration.

12. The method according to claim 1, wherein the method comprises virtually designing the emergence profile of the customized healing abutment from the top of the implant to the beginning of the gingiva.

13. The method according to claim 1, wherein the method comprises using the shape of the original tooth to design the customized healing abutment.

14. The method according to claim 1, wherein the designed customized healing abutment comprises a substantially flat, rounded off top.

15. The method according to claim 1, wherein the information relates to the height of the implant screw head, and wherein the opening of the customized healing abutment is shaped to provide that the transition from the customized healing abutment to the implant screw is smooth.

16. The method according to claim 2, wherein the method comprises virtually planning the surgical drilling of the bore for the implant.

17. The method according to claim 16, wherein the virtual planning of the surgical drilling and/or virtual design of the drill guide is/are designed based on the 3D surface scan and/or on the 3D internal scan.

18. The method according to claim 1, wherein the method comprises virtually extracting any teeth which are placed where an implant is planned to be arranged.

19. The method according to claim 1, wherein the method comprises virtually designing the soft tissue surrounding the customized healing abutment.

20. The method according to claim 1, wherein the 3D internal scan is a CT scan.

21. The method according to claim 20, wherein the CT scan is a cone-beam CT scan (CBCT scan).

22. The method according to claim 1, wherein virtually placing the implant and virtually designing the customized healing abutment are performed as part of an iterative process where each iteration of the iterative process comprises evaluating the implant placement and/or the customized healing abutment design and based on a result of the evaluation determining whether the implant placement and/or the customized healing abutment design must be modified.

23. The method according to claim 22, where the evaluation of the iterative process takes into account the design of the final restoration.

24. The method according to claim 7, where the implant placement is modified based on the designed customized healing abutment and/or based on the designed final restoration.

25. The method according to claim 7, wherein the customized healing abutment is redesigned based on the modified implant placement and/or based on the designed final restoration.

26. The method according to claim 22, where the drill guide is virtually designed based on the planned implant placement after the last iteration of the iterative process.

27. The method according to claim 1, wherein the final restoration is a crown, bridge, or denture.

28. A kit comprising a customized healing abutment and a drill guide for a patient, where the kit comprises;
    a drill guide for guiding the surgical drilling of a bore for the implant into the patient's jaw bone at the planned implant placement; and
    a customized healing abutment configured for shaping the soft tissue according to a target profile when arranged in the implant,
where the drill guide and customized healing abutment are designed according to the method of claim 1,
    where the drill guide and customized healing abutment are configured to provide that an implant arranged in a bore drilled using the drill guide is placed at the planned implant placement such that the customized healing abutment can shape the soft tissue according to the target profile when arranged in the implant.

29. The method according to claim 1, wherein the second scan is taken of the patient's actual jaw after the healing is finished.

* * * * *